US010724903B2

(12) United States Patent
Chen et al.

(10) Patent No.: US 10,724,903 B2
(45) Date of Patent: Jul. 28, 2020

(54) POLYMER ENCAPSULATED PARTICLES AS SURFACE ENHANCED RAMAN SCATTERING PROBES

(75) Inventors: Hongyu Chen, Singapore (SG); Miaoxin Yang, Singapore (SG); Jun Xu, Singapore (SG); Yuhua Feng, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 295 days.

(21) Appl. No.: 12/994,006

(22) PCT Filed: May 22, 2009

(86) PCT No.: PCT/SG2009/000181
§ 371 (c)(1),
(2), (4) Date: Mar. 14, 2011

(87) PCT Pub. No.: WO2009/142604
PCT Pub. Date: Nov. 26, 2009

(65) Prior Publication Data
US 2011/0151586 A1    Jun. 23, 2011

Related U.S. Application Data

(60) Provisional application No. 61/055,583, filed on May 23, 2008.

(51) Int. Cl.
| G01N 21/65 | (2006.01) |
| G01N 33/545 | (2006.01) |
| B05D 3/00 | (2006.01) |
| G01J 3/44 | (2006.01) |
| G01N 33/532 | (2006.01) |
| G01N 33/553 | (2006.01) |
| B82Y 15/00 | (2011.01) |
| B22F 1/00 | (2006.01) |

(52) U.S. Cl.
CPC ............. *G01J 3/44* (2013.01); *B22F 1/0062* (2013.01); *B82Y 15/00* (2013.01); *G01N 21/658* (2013.01); *G01N 33/532* (2013.01); *G01N 33/553* (2013.01); *B22F 2998/00* (2013.01); *B22F 2998/10* (2013.01)

(58) Field of Classification Search
CPC B22F 1/0062; B22F 2998/00; B22F 2998/10; B22F 1/0018; B22F 2202/17; B82Y 15/00; G01J 3/44; G01N 21/658; G01N 33/532; G01N 33/553
See application file for complete search history.

(56) References Cited

U.S. PATENT DOCUMENTS

| 6,509,128 B1 * | 1/2003 | Everaerts ................... C09J 5/00 430/111.4 |
| 6,514,767 B1 | 2/2003 | Natan ........................... 436/166 |
| 2002/0045045 A1 * | 4/2002 | Adams et al. ................. 428/403 |
| 2005/0089901 A1 * | 4/2005 | Porter .................... C07H 21/02 435/6.11 |
| 2005/0217424 A1 | 10/2005 | Natan ............................. 75/332 |
| 2006/0073336 A1 | 4/2006 | Zhang et al. ................. 428/407 |
| 2007/0072309 A1 | 3/2007 | Pris et al. ..................... 436/524 |
| 2007/0165219 A1 | 7/2007 | Natan et al. .................. 356/301 |

FOREIGN PATENT DOCUMENTS

| CA | 2 551 130 A1 | 7/2005 |
| WO | WO 2009/038544 A1 | 3/2009 |

OTHER PUBLICATIONS

Afara et al., "Comparison of Raman scattering from local and coupled modes of small uniformly coated spheres," J. Chem. Phys., 1989, vol. 90, No. 2, pp. 713-728.*
A print-out retrieved from https://en.wikipedia.org/wiki/Ethanethiol on Apr. 10, 2017.*
A printout "4-Mercaptobenzoic acid" retrieved from https://www.sigmaaldrich.com/catalog/product/aldrich/706329?lang=en&region=US on Jul. 24, 2018.*
A printout "Tripropylphosphine oxide" retrieved from http://www.chemspider.com/Chemical-Structure.66531.html on Mar. 20, 2019.*
van Vegten et al., "Chemisorption of methyl mercaptane on titania-supported Au nanoparticles: Viability of Au surface area determination," J. Colloid Interface Sci., 2009, vol. 339, issue 2, pp. 310-316.*
Alvarez-Puebla et al., "Surface-enhanced Raman scattering for ultrasensitive chemical analysis of 1 and 2-naphthalenethiols," *The Analyst* 129:1251-1256, 2004.
Banholzer et al., "Rationally designed nanostructures for surface-enhanced Raman spectroscopy," *Chem. Soc. Rev.* 37:885-897, 2008.
Campion et al., "Surface-enhanced Raman scattering," *Chemical Society Reviews* 27:241-250, 1998.
Cao et al., "Nanoparticles with Raman Spectroscopic Fingerprints for DNA and RNA Detection," *Science* 297:1536-1540, 2002.
Chen et al., "Encapsulation of Single Small Gold Nanoparticles by Diblock Copolymers," *ChemPhysChem* 9:388-392, 2008.
Doering et al., "Spectroscopic Tags Using Dye-Embedded Nanoparticles and Surface-Enhanced Raman Scattering," *Analytical Chemistry* 75(22):6171-6176, 2003.
Doering et al., "SERS as a Foundation for Nanoscale, Optically Detected Biological Labels," *Adv. Mater.* 19:3100-3108, 2007.
Driskell et al., "Low-Level Detection of Viral Pathogens by a Surface-Enhanced Raman Scattering Based Immunoassay," *Analytical Chemistry* 77(19):6147-6154, 2005.

(Continued)

*Primary Examiner* — Galina M. Yakovleva
(74) *Attorney, Agent, or Firm* — Seed IP Law Group LLP

(57) ABSTRACT

The present invention refers to a Raman active composite material comprising a metal particle; a coating layer of a Raman active molecule bound to the metal particle; and an encapsulating layer of an amphiphilic polymer bound to the metal particle. The present invention also refers to methods of manufacturing a Raman active composite material described herein and their uses.

19 Claims, 18 Drawing Sheets

(56) References Cited

OTHER PUBLICATIONS

Duan et al., "Cell-Penetrating Quantum Dots Based on Multivalent and Endosome-Disrupting Surface Coatings," *J. Am. Chem. Soc.* 129:3333-3338, 2007.

Freeman et al., "Detection of biomolecules using nanoparticle, surface enhanced Raman scattering tags," *Nanoparticles and Biomedical Applications II, Proceedings of SPIE* 5705:114-122, 2005.

Frens, "Controlled Nucleation for the Regulation of the Particle Size in Monodisperse Gold Suspensions," *Nature Physical Science* 241:20-22, 1973.

Graham et al., "Quantitative SERRS for DNA sequence analysis," *Chem. Soc. Rev.* 37:1042-1051, 2008.

Haynes et al., "New substrates and single-molecule detection are just two of the advances that are fueling interest in SERS. Surface-Enhanced Raman Spectroscopy," *Analytical Chemistry* 77:338A-346A, 2005.

He et al., "Surface-Enhanced Raman Scattering: A Structure-Specific Detection Method for Capillary Electrophoresis," *Analytical Chemistry* 72(21):5348-5355, 2000.

Hoshino et al., "Physicochemical Properties and Cellular Toxicity of Nanocrystal Quantum Dots Depend on Their Surface Modification," *Nano Letters* 4(11):2163-2169, 2004.

Hu et al., "Mammalian Cell Surface Imaging with Nitrile-Functionalized Nanoprobes: Biophysical Characterization of Aggregation and Polarization Anisotrophy in SERS Imaging," *J. Am. Chem. Soc.* 129:14-15, 2007.

Kang et al., "Core/Shell Gold Nanoparticles by Self-Assembly and Crosslinking of Micellar, Block-Copolymer Shells," *Angew. Chem. Int. Ed.* 44:409-412, 2005.

Kang et al., "Controlling Shell Thickness in Core-Shell Gold Nanoparticles via Surface-Templated Adsorption of Block Copolymer Surfactants," *Macromolecules* 38:6115-6121, 2005.

Kim et al., "Magnetomicelles: Composite Nanostructures from Magnetic Nanoparticles and Cross-Linked Amphiphilic Block Copolymers," *Nano Letters* 5(10):1987-1991, 2005.

King et al., "Quantum Dots—Utilization in TEM," *Microsc Microanal* 14(Suppl. 2):702-703, 2008.

Kneipp, "Nanosensors Based on SERS for Applications in Living Cells," *Surface-Enhanced Raman Scattering—Physics and Applications, Topics Appl. Phys.* 103:335-350, 2006.

Kneipp et al., "Ultrasensitive Chemical Analysis by Raman Spectroscopy," *Chem. Rev.* 99:2957-2975, 1999.

Lee et al., "Biological Imaging of HEK293 Cells Expressing PLCγ1 Using Surface-Enhanced Raman Microscopy," *Analytical Chemistry* 79(3):916-922, 2007.

Love et al., "Self-Assembled Monolayers of Thiolates on Metals as a Form of Nanotechnology," *Chem. Rev.* 105:1103-1169, 2005.

McCabe et al., "SERRS labelled beads for multiplex detection," *Faraday Discuss.* 132:303-308, 2006.

Mulvaney et al., "Glass-Coated, Analyte-Tagged Nanoparticles: A New Tagging System Based on Detection with Surface-Enhanced Raman Scattering," *Langmuir* 19:4784-4790, 2003.

Nikoobakht et al., "Preparation and Growth Mechanism of Gold Nanorods (NRs) Using Seed-Mediated Growth Method," *Chem. Mater.* 15:1957-1962, 2003.

Njoki et al., "Size Correlation of Optical and Spectroscopic Properties for Gold Nanoparticles," *J. Phys. Chem. C* 111:14664-14669, 2007.

Porter et al., "SERS as a bioassay platform: fundamentals, design, and applications," *Chem. Soc. Rev.* 37:1001-1011, 2008.

Qian et al., "Single-molecule and single-nanoparticle SERS: from fundamental mechanisms to biomedical applications," *Chem. Soc. Rev.* 37:912-920, 2008.

Qian et al., "In vivo tumor targeting and spectroscopic detection with surface-enhanced Raman nanoparticle tags," *Nature Biotechnology* 26(1):83-90, 2008.

Shen et al., "Morphological Phase Diagram for a Ternary System of Block Copolymer $PS_{310}$-b-$PAA_{52}$/Dioxane/$H_2O$," *J. Phys. Chem. B* 103:9473-9487, 1999.

Siekkinen et al., "Rapid synthesis of small silver nanocubes by mediating polyol reduction with a trace amount of sodium sulfide or sodium hydrosulfide," *Chemical Physics Letters* 432:491-496, 2006.

Stewart et al., "Nanostructured Plasmonic Sensors," *Chem. Rev.* 108:494-521, 2008.

Su et al., "Composite Organic-Inorganic Nanoparticles (COINs) with Chemically Encoded Optical Signatures," *Nano Letters* 5(1):49-54, 2005.

Sun et al., "Composite Organic-Inorganic Nanoparticles as Raman Labels for Tissue Analysis," *Nano Letters* 7(2):351-356, 2007.

Terreau et al., "Effect of Poly(acrylic acid) Block Length Distribution on Polystyrene-b-poly(acrylic acid) Block Copolymer Aggregates in Solution. 2. A Partial Phase Diagram," *Langmuir* 20:637-645, 2004.

Willets et al., "Localized Surface Plasmon Resonance Spectroscopy and Sensing," *Annu. Rev. Phys. Chem.* 58:267-297, 2007.

Zhang et al., "Multiple Morphologies and Characteristics of "Crew-Cut" Micelle-like Aggregates of Polystyrene-b-poly(acrylic acid) Diblock Copolymers in Aqueous Solutions," *J. Am. Chem. Soc.* 118:3168-3181, 1996.

Zhang et al., "Controlling the Growth of Charged-Nanoparticle Chains through Interparticle Electrostatic Repulsion," *Angew. Chem. Int. Ed.* 47:3984-3987, 2008.

\* cited by examiner

A)

B)

C)

D)

E)

F)

G)

H)

I)

J)

K)

L)

M)

N)

O)

P)

Q)

R)

S)

T)

U)

POLYMER ENCAPSULATED PARTICLES AS SURFACE ENHANCED RAMAN SCATTERING PROBES

CROSS-REFERENCE TO RELATED APPLICATIONS

This application claims benefit of priority of U.S. provisional application No. 61/055,583, filed May 23, 2008, the contents of it being hereby incorporated by reference in its entirety for all purposes.

FIELD OF THE INVENTION

The present invention relates to the field of biochemistry, in particular to the field of biochemical labels and surface chemistry.

BACKGROUND OF THE INVENTION

In recent years, surface-enhanced Raman scattering (SERS) labels are becoming more important as an alternative to fluorescent labels.

The effect of Raman scattering occurs when a beam of light interacts with a molecule, not an atom. Part of the incident light is reflected, and part of it is scattered. Over 99% of the scattered radiation has the same frequency as the incident beam and is called Mie and Rayleigh scattering. However, a small portion of the scattered radiation has frequencies different from that of the incident beam and is called Raman and Brilliouin scattering which forms of inelastic scattering. The frequency differences between the incident and inelastically scattered radiation are determined by the properties of the molecules of which the material under study is made and are characteristic for every molecule, like a fingerprint. The Raman scattered radiation has energies slightly less than the incident photon (Stokes shift). Those energies correspond to some of the various vibrations and/or rotations of the target molecule. The Raman spectrum for a given molecule in a given environment is always the same irrespective of the frequency of the incident light. This is in contrast to fluorescence which absorbs light when the frequency or photon energy matches the energy difference between two energy levels of the molecule.

The use of Raman Scattering to investigate molecules absorbed on surfaces was initially thought to be of insufficient sensitivity. However, it was discovered that certain molecules and metal surfaces could display Raman scattering cross-sections many orders of magnitude greater than for isolated molecules. Increases in the intensity of Raman signal have been regularly observed on the order of $10^4$-$10^6$, and can be as high as $10^8$ and $10^{14}$. The importance of SERS is that it is both surface selective and highly sensitive where as Raman scattering is neither. The phenomenon of SERS is generally explained by a combination of an electromagnetic (EM) mechanism describing the surface electron movement in the substrate, such as a metal particle, and a chemical mechanism related to charge transfer (CT) between the substrate and a Raman active molecule.

For the chemical enhancement process, it is thought that the metal of the metal particle aids in CT excitations between the highest occupied molecular orbital (HOMO) and the lowest unoccupied molecular orbital (LUMO) of the adsorbate, i.e. the molecule bound to the surface. These excitations are possible if the Fermi level of the metal is approximately halfway between the HOMO and LUMO of the adsorbate, which in turn allows CT processes to occur at approximately half the energy of the inherent intramolecular excitations. Naturally, this effect varies from molecule to molecule, but because the energetically lowest-lying CT process is in the near ultraviolet for most organic molecules, this metal-aided process occurs in the visible spectrum.

Known nanometer-sized SERS labels usually consist of a coating layer of Raman reporter molecules on the surface of metal nanoparticles (metal NPs) which act as the source of enhancement. Compared with fluorescent labels, Raman reporters on metal NPs are resistant to photo-bleaching owing to the quenching of fluorescence excited states by metal surface and to the short lifetime of Raman virtual energy states. In addition, multiple reporters can be excited with a single light source of choice (such as near infrared light for human tissue), giving multiple sets of narrow peaks characteristic of the individual reporters. They might therefore be usable for applications in various biomedical systems.

Direct attachment of Raman reporters to metal NPs is a known technique. However, the efficiency and reliability of the nanoprobes are often compromised by ligand dissociation or exchange and the exposed Raman reporters would be easily influenced by variations in chemical or biological environments. A variety of encapsulation methods were, therefore, developed to enhance the stability of the nanoprobes, by coating them with biomolecules (such as bovine serum albumin), PEG-SH, or inorganic layers (such as $SiO_2$).

While all these approaches reduce the dissociation of Raman reporters and provide secure anchoring points for labelling, the silica-coated nanoprobes were shown to be superior as they were impermeable to dye molecules, remarkably stable in salt media and in organic solvents, and their signals unaffected by the attachment of biomolecules (Mulvaney, S. P., Musick, M. D., et al., 2003, Langmuir, vol. 19, pp. 4784). Unlike surface-adsorbed biomolecules or ligands, the $SiO_2$ shell is chemically stable and does not dissociate. More importantly, a well-defined core/shell structure provides unambiguous composition of the nanoprobes with minimal overall diameter, as opposed to NP aggregates with nonspecific sizes.

The growth of $SiO_2$ shell on metal NPs typically require two types of ligands, one as the Raman reporter and one to make the metal surface amenable to $SiO_2$ attachment. This requirement leads to multiple problems in designing SERS labels. The vitreophilic (glass loving) molecules are typically $NH_2$- or SH-ended silanes while the Raman reporters typically have aromatic groups. These two types of ligands do not naturally mix and there is no known Raman reporter that is vitrophilic. So far, only limited number of reporters has been shown to be compatible with the $SiO_2$ coating. Segregation of the two types of ligands could occur and lead to non-uniform distribution of the reporter molecules among the individual NPs. Furthermore, only a small fraction of the metal surface are available for Raman reporter molecules, or otherwise $SiO_2$ would not be able to form a continuous shell on the metal NPs. The low surface concentration of Raman reporter inevitably leads to weak SERS signals. The growth of $SiO_2$ layer is another source of problems. Since it is kinetically controlled, the shell thickness depends on the growth conditions and is not intrinsically uniform. The growth conditions need to be precisely controlled and it was also required to avoid the formation of pure silica particles and the aggregation of the NPs. Typical syntheses in this system requires more than 30 h of complicated procedures such as dialysis and ion-exchange.

Therefore, it is an object of the present invention to provide alternative Raman active labels which overcome some of the above problems.

SUMMARY OF THE INVENTION

In a first aspect, the present invention is directed to a Raman active composite material comprising:
- a metal particle;
- a coating layer of a Raman active molecule bound to the metal particle; and
- an encapsulating layer of an amphiphilic polymer bound to the metal particle.

In a further aspect, the present invention is directed to a method of manufacturing a Raman active composite material described herein, wherein the method comprises:
- incubating a metal particle with a Raman active molecule and an organic solvent in a first solution;
- adding an amphiphilic polymer to the first solution;
- heating the first solution after adding the amphiphilic polymer; and
- cooling the first solution.

In a further aspect, the present invention refers to a method of manufacturing an anisotropically encapsulated Raman active composite material, wherein the method comprises:
- providing a solution comprising a metal particle, an organic solvent, an amphiphilic polymer, a ligand comprising a binding moiety for binding to the metal particle and a Raman active molecule;
- incubating the solution for a time sufficient to allow self-assembly of an amphiphilic polymer shell around the metal particle; and
- cooling the solution.

In another aspect, the present invention refers to the use of a Raman active composite material according as described herein or a Raman active composite material obtained by a method described herein for detection and/or labelling of analytes.

In a further aspect, the present invention refers to a Raman active composite material obtained by a method described herein.

BRIEF DESCRIPTION OF THE DRAWINGS

The invention will be better understood with reference to the detailed description when considered in conjunction with the non-limiting examples and the accompanying drawings, in which:

FIG. 1 shows an amphiphilic polymer wherein the dotted line stands for the hydrophilic portion of the amphiphilic polymer while the solid line stands for the hydrophobic portion of the amphiphilic polymer.

FIG. 7 shows the SERS signals of AuNPs coated with the Raman active molecules shown in FIG. 6 and encapsulated with an amphiphilic polymer in water.

FIGS. 9A, B and C show the anisotropic encapsulation of nanospheres. FIG. 9D shows the encapsulation of several nanospheres in a chain, wherein a portion of two of the five nanospheres (the third and fifth from the left) are not encapsulated not only in the contact area between the nanoparticles but also in portions facing the external environment. FIG. 9E shows the anisotropic encapsulation of a nanorod while FIG. 9F shows the anisotropic encapsulation of a nanocube. FIGS. 9A' and B' show the corresponding TEM images of gold nanoparticles as illustrated in FIGS. 9A and B, respectively (scale bars 50 nm).

FIG. 10A shows AuNPs coated with 2-naphthalenethiol as Raman active molecule and ethanethiol as ligand comprising a binding moiety for binding to the metal nanoparticle, and partially encapsulated with $PS_{154}$-block-$PAA_{60}$ (ratio of ethanethiol to 2-naphthalenethiol=7.41; incubation time and temperature for self assembly of polymer shell: 150° C., 3 h). FIG. 10B shows AuNPs coated with 4-ethylthiophenol as Raman active molecule and ethanethiol as ligand comprising a binding moiety for binding to the metal nanoparticle, and partially encapsulated with $PS_{154}$-block-$PAA_{60}$ (ratio of ethanethiol to 4-ethylthiophenol=2.40; incubation time and temperature for self assembly of polymer shell: 130° C., 6 h). FIG. 10C shows anisotropically encapsulated AuNP chains coated with 2-naphthalenthiol (Raman active molecule) and ethanethiol (ligand comprising a binding moiety for binding to the metal nanoparticle).

DETAILED DESCRIPTION OF THE INVENTION

Figure 1:
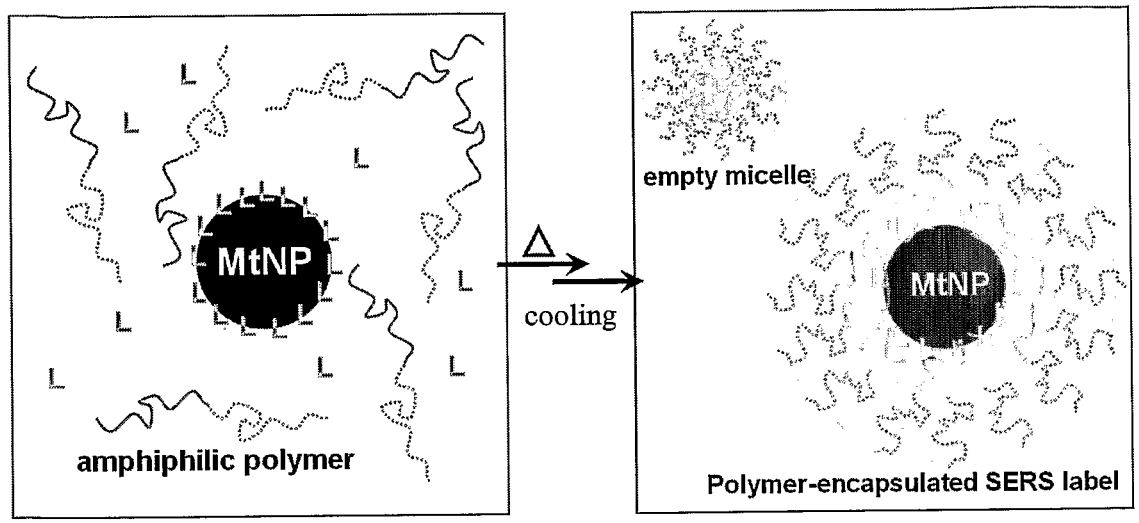
FIG. 1 shows the preparation of polymer-encapsulated metal NPs (MtNPs) by self-assembly. It is a one-pot synthesis involving the heating of MtNPs with hydrophobic Raman active molecules (L) and amphiphilic polymers, such as $PS_{154}$-block-$PAA_{60}$ followed by gradual cooling.

In a first embodiment, the present invention is directed to a Raman active composite material comprising:
 a metal particle;
 a coating layer of a Raman active molecule bound to the metal particle; and
 an encapsulating layer of an amphiphilic polymer bound to the metal particle.

Such Raman active composite materials have been shown to be stable in test in which they have been exposed to adverse conditions. For example, salt medium was known to cause aggregation of citrate-stabilized AuNPs, as the increased ionic strength weakens the charge-repulsion between the NPs. In contrast, the Raman active composite material described herein can tolerate up to 0.1 M NaCl without aggregation. No change of SERS intensity was observed with and without the salt media. This allows the use of these Raman active composite materials in buffer solutions often encountered in biomedical applications. The amphiphilic polymer forms a polymer shell around the metal particle which is coated with a Raman active molecule and thus provides protection against chemical oxidation as demonstrated in the experimental section of this application.

A "Raman active molecule" refers to a molecule which exhibits a characteristic Raman spectrum upon excitation with light. In general, the Raman spectrum is independent of the wavelength of the excitation light, but near-infrared (i.e. 750 nm to about 100 μm) excitation is most favourable for bio-detection owing to the small absorption of near-infrared light by tissue. Due to the binding of the Raman active molecule to a metal particle, the Raman signal is greatly enhanced which means that the Raman active composite material is a Surface Enhanced Raman Scattering (SERS) active composite material. The Raman active composite material referred to herein is characterized by an increase in the intensity of the Raman signal emitted by the Raman active molecules.

Examples for Raman active molecules can include, but are not limited to

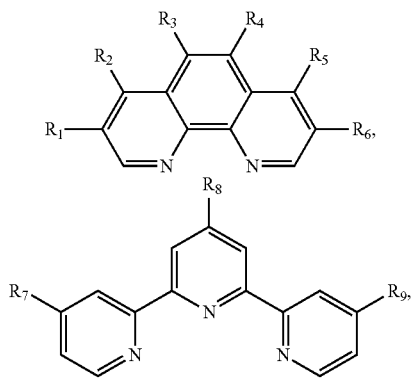

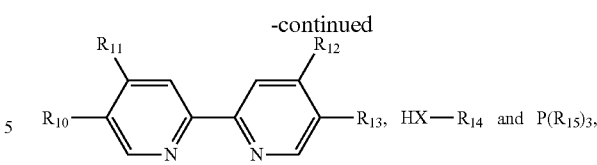

wherein $R_1$ to $R_{13}$ are independently selected from hydrogen, alkyl, optionally substituted alkyl, optionally substituted aryl, alkoxy, aryl, halogen, $NO_2$, CN, OH, carbonyl (—C=O)) or amino (—$NH_2$); $R_{14}$ to $R_{15}$ are selected from optionally substituted alkyl, alkoxy, optionally substituted aryl and optionally substituted aryloxy; X is S or O. Because the Raman spectrum reflects the vibrational energy levels of a particular molecule, any small change in the molecular structure, including the peripheral substituent groups, can cause changes in the energy levels and thus lead to changes in the Raman fingerprint.

The term "alkyl", alone or in combination, refers to a fully saturated aliphatic hydrocarbon. In certain embodiments, alkyls are optionally substituted. In certain embodiments, an alkyl comprises 1 to 30 carbon atoms, for example 1 to 20 carbon atoms, wherein (whenever it appears herein in any of the definitions given below) a numerical range, such as "1 to 20" or "$C_1$-$C_{20}$", refers to each integer in the given range, e.g. "$C_1$-$C_{20}$ alkyl" means that an alkyl group comprising only 1 carbon atom, 2 carbon atoms, 3 carbon atoms, etc., up to and including 20 carbon atoms. Examples of alkyl groups include, but are not limited to, methyl, ethyl, n-propyl, isopropyl, n-butyl, isobutyl, sec-butyl, tert-butyl, tert-amyl, pentyl, hexyl, heptyl, octyl and the like.

The term "alkoxy", alone or in combination, refers to an aliphatic hydrocarbon having an alkyl-O— moiety. In certain embodiments, alkoxy groups are optionally substituted. Examples of alkoxy groups include, but are not limited to, methoxy, ethoxy, propoxy, butoxy and the like.

The term "aliphatic", alone or in combination, refers to a straight chain or branched chain hydrocarbon comprising at least one carbon atom. Aliphatics include alkyls, alkenyls, and alkynyls. In certain embodiments, aliphatics are optionally substituted. Aliphatics include, but are not limited to, methyl, ethyl, propyl, isopropyl, butyl, isobutyl, tert-butyl, pentyl, hexyl, ethenyl, propenyl, butenyl, ethynyl, butynyl, propynyl, and the like, each of which may be optionally substituted. As used herein, aliphatic is not intended to include cyclic groups.

The term "alkyne", alone or in combination, refers to an aliphatic hydrocarbon having one or more carbon-carbon triple-bonds. In certain embodiments, alkyne groups are optionally substituted. Examples of alkyne groups include, but are not limited to, ethynyl, propynyl, butynyl, and the like.

The term "alkene", alone or in combination, refers to an aliphatic hydrocarbon having one or more carbon-carbon double-bonds. In certain embodiments, alkene groups are optionally substituted. Examples of alkene groups include, but are not limited to, ethenyl, propenyl, butenyl, 1,4-butadienyl, pentenyl, hexenyl, 4-methylhex-1-enyl, 4-ethyl-2-methylhex-1-enyl and the like.

The term "haloaliphatic", alone or in combination, refers to an aliphatic hydrocarbon in which at least one hydrogen atom is replaced with a halogen atom. In certain embodiments in which two or more hydrogen atoms are replaced with halogen atoms, the halogen atoms are all the same. In certain embodiments, the halogen atoms are not all the same, but differ from each other. Haloaliphatic groups include haloalkyls, haloalkenyls, and haloalkynyls. In certain embodiments, haloaliphatics are optionally substituted, in addition to the hydrogen/halogen substitution. The term "haloaliphatic" also includes perhaloaliphatic, in which all of the hydrogen atoms of the aliphatic hydrocarbon are replaced by halogen atoms. Examples of perhaloaliphatics include, but are not limited to, trichloromethyl, pentacholorethyl, and the like.

The term "aryl" refers to an aromatic ring wherein each of the atoms forming the ring is a carbon atom. Aryl rings may be formed by five, six, seven, eight, nine, or more than nine carbon atoms. Aryl groups may be optionally substituted.

The term "aromatic" refers to a group comprising a covalently closed planar ring having a delocalized π-electron system comprising 4n+2 π-electrons, where n is an integer-aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon, atoms, and optionally carrying one or more substituents selected from an aryl, a heteroaryl, a cycloalkyl, a nonaromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyallcyl, a $C_{1-6}$ aminoalkyl, a $C_{1-6}$ alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylph.enyl, and 4-(2-oxopyrrolidin-1-yl)phenyl.

The term "heterocycle" refers to a group comprising a covalently closed ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom. Examples of heterocycles include, but are not limited to the following:

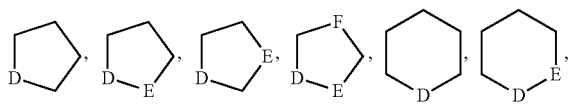

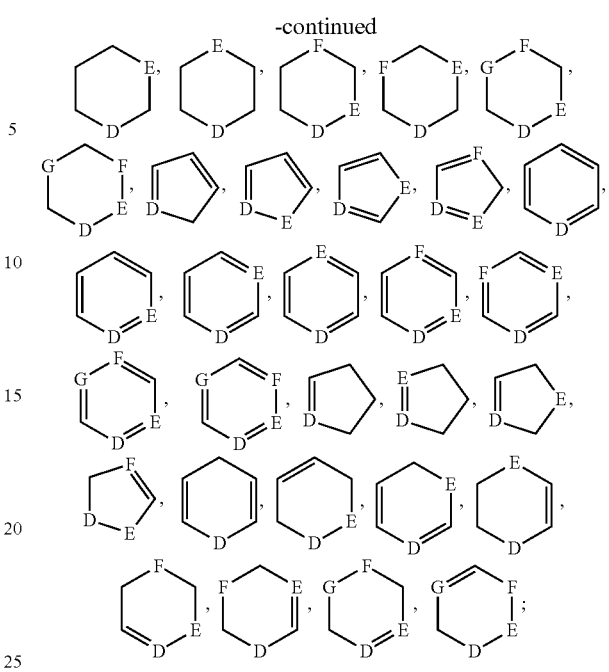

wherein D, E, F, and G independently represent a heteroatom. Each of D, E, F, and G may be the same or different from one another.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "non-aromatic ring" refers to a group comprising a covalently closed ring that is not aromatic.

The term "heteroaryl" refers to an aromatic heterocycle. Heteroaryl rings may be formed by three, four, five, six, seven, eight, nine, or more than nine atoms. Heteroaryls may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoallcyl, alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings may be optionally substituted. Rings may form part of a ring system.

The term "ring system" refers to two or more rings, wherein two or more of the rings are fused. The term "fused" refers to structures m which two or more rings share one or more bonds.

The term "optionally substituted" refers to a group in which none, one, or more than one of the hydrogen atoms has been replaced with one or more group(s) are independently selected from: alkyl, heteroalkyl, haloalkyl, heteroholoalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups. In embodiments in which two or more hydrogen atoms have been substituted, the substituent groups may be linked to form a ring.

The term "O-carboxy" refers to a group of formula RC(=O)O—.

The term "C-carboxy" refers to a group of formula —C(=O)OR.

The term "acetyl" refers to a group of formula —C(=O)CH$_3$.

The term "trihalomethanesulfonyl" refers to a group of formula $X_3CS(=O)^2$— where X is a halogen. A "halogen" is either F, or Cl, or Br, or I.

The term "cyano" refers to a group of formula —CN.

The term "isocyanato" refers to a group of formula —NCO.

The term "thiocyanato" refers to a group of formula —CNS.

The term "isothiocyanato" refers to a group of formula —NCS.

The term "sulfonyl" refers to a group of formula —S(=O)—R.

The term "S-sulfonamido" refers to a group of formula —S(=O)$_2$NR.

The term "N-sulfonamido" refers to a group of formula RS(=O)$_2$NH—.

The term "trihalomethanesulfonamido" refers to a group of formula $X_3CS(=O)_2NR$—.

The term "O-carbamyl" refers to a group of formula —OC(=O)—NR.

The term "N-carbamyl" refers to a group of formula ROC(=O)NH—.

The term "O-thiocarbamyl" refers to a group of formula —OC(=S)—NR.

The term "N-thiocarbamyl" refers to a group of formula ROC(=S)NH—.

The term "C-amido" refers to a group of formula —C(=O)—NR$_2$.

The term "N-amido" refers to a group of formula RC(=O)NH—.

The term "ester" refers to a chemical moiety with formula —(R)$_n$-COOR', where R and R' are independently selected from the group which includes, but is not limited to alkyl, cycloalkyl, aryl, heteroaryl (bonded through a ring carbon) or non-aromatic heterocycle (bonded through a ring carbon), where n is 0 or 1.

The term "amide" refers to a chemical moiety with formula —(R)$_n$C(O)NHR' or —(R)$_n$—NHC(O)R', where R and R' are independently selected from the group which includes, but is not limited to alkyl, cycloalkyl, aryl, heteroaryl (bonded through a ring carbon) or heteroalicyclic (bonded through a ring carbon), where n is 0 or 1. In certain embodiments, an amide may be an amino acid or a peptide.

The terms "amine," "hydroxy," and "carboxyl" include such groups that have been esterified or amidified. Procedures and specific groups used to achieve esterification and amidification are known to those of skill in the art.

In one embodiment, the Raman active molecule includes, but is not limited to

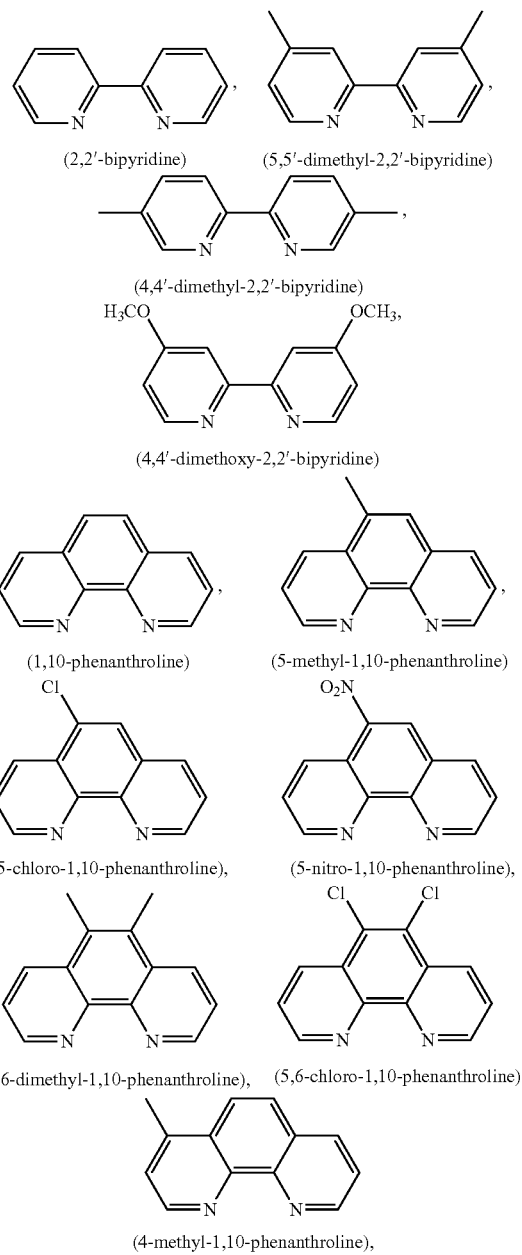

-continued

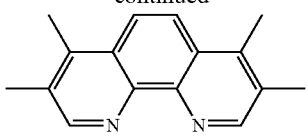
(3,4,7,8-tetramethyl-1,10-phenanthroline),

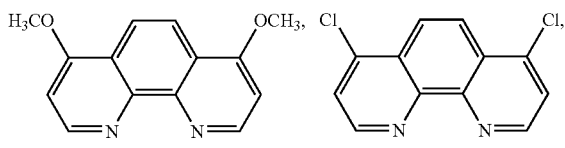
(4,7-dimethoxy-1,10-phenanthroline)    (4,7-chloro-1,10-phenanthroline)

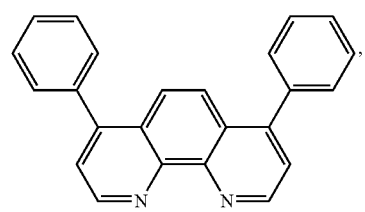
(4,7-phenyl-1,10-phenanthroline)

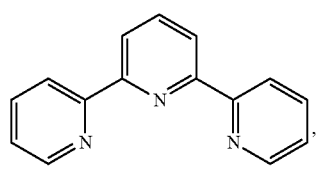
(2,2';6',2''-terpyridine)

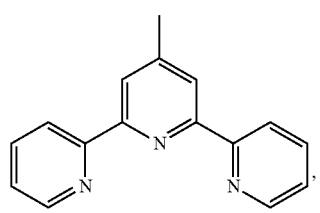
(4-methyl-2,2';6',2''-terpyridine)

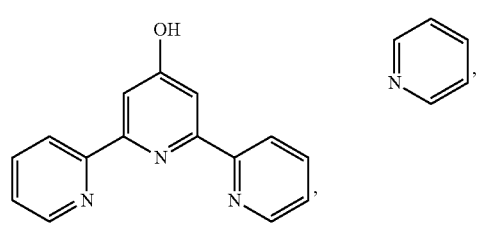
(4-hydroxy-2,2';6',2''-terpyridine)

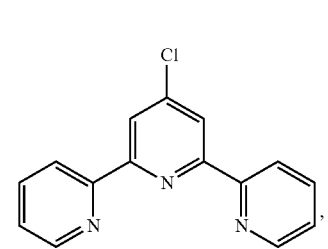
(4-chloro-2,2';6',2''-terpyridine)

-continued

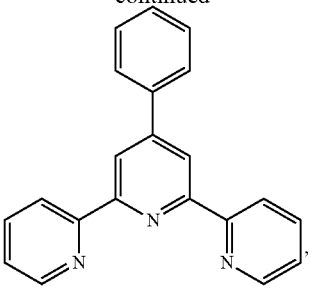
(4-phenyl-2,2';6',2''-terpyridine)

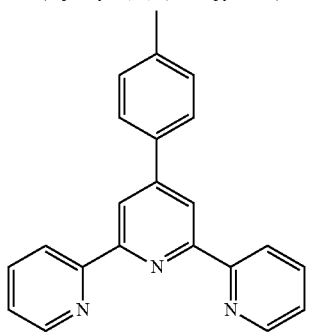
(4'(4-methyl-phenyl-2,2';6',2''-terpyridine),

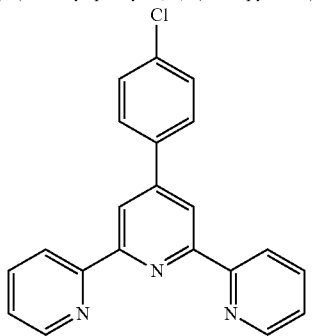
(4'(4-chloro-phenyl-2,2';6',2''-terpyridine),

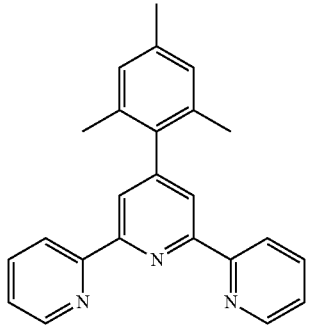
(4'-(2,4,6-trimethyl-phenyl-2,2';6',2''-terpyridine),

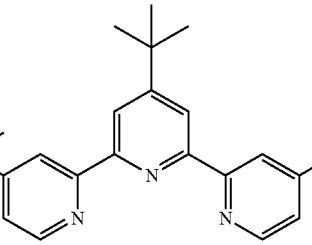
(4,4',4''-tri-tert-butyl-2,2';6',2''-terpyridine)

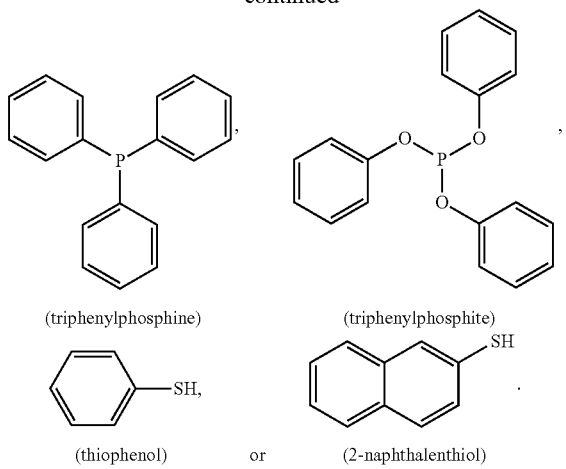

(triphenylphosphine)   (triphenylphosphite)

(thiophenol)   or   (2-naphthalenthiol)

In one embodiment derivatives of 1,10-phenanthroline are used as Raman active molecules. Derivatives of 1,10-phenanthroline can include but are not limited to 5,6-dimethyl-1,10-phenanthroline, 4,7-dimethoxy-1,10-phenanthroline, 4,7-dichloro-1,10-phenanthroline, 5-chloro-1,10-phenanthroline, 4,7-chloro-1,10-phenanthroline, 4,7-phenyl-1,10-phenanthroline, 3,4,7,8-tetramethyl-1,10-phenanthroline, 5-methyl-1,10-phenanthroline, 5-nitro-1,10-phenanthroline, 4-methyl-1,10-phenanthroline or batho-1,10-phenanthroline.

In one embodiment derivatives of 2,2'-bipyridine are used as Raman active molecules. Derivatives of 2,2'-bipyridine can include but are not limited to 4,4'-dimethoxy-2,2'-bipyridine, 5,5'-dimethyl-2,2'-bipyridine and 4,4'-dimethyl-2,2'-bipyridine.

In one embodiment derivatives of 2,2';6',2"-terpyridine are used as Raman active molecules. Derivatives of 2,2';6',2"-terpyridine can include but are not limited to 4'(4-methylphenyl)-2,2';6,2"-terpyridine, 4-chloro-2,2';6',2"-terpyridine, 4,4',4"-tri-tert-buthyl-2,2';6',2"-terpyridine, 4-phenyl-2,2';6',2"-terpyridine, 4-hydroxy-2,2';6',2"-terpyridine, 4'(4-nitro-phenyl-2,2';6',2"-terpyridine and 2,6-bis(2-pyridyl)-4(1H)-pyridone.

The inventors found that Raman active molecules as described above can bind to the surface of the metal particle even those molecules which do not provide a thiol group, such as triphenylphosphine or 1,10-phenanthroline. Raman active molecules comprising a moiety with an affinity for the surface of the metal particle can be used. Such moieties can include but are not limited to thiols, amines, phosphines, phosphine oxides, and any combination thereof. The Raman active molecules render the metal particles hydrophobic and form a first uniform layer around the metal particle. To protect this first layer of Raman active molecules from dissociation and degradation the metal particle is encapsulated with an amphiphilic polymer.

In general, any amphiphilic polymer can be used in the present invention as long as the polymer self-assembles in solution so that the hydrophobic portions face the metal particle and the hydrophilic portions face the solution. Such an arrangement is based on the solvophobic interactions between the hydrophobic Raman active molecules coating metal particles and hydrophobic polymer portion. Furthermore, the hydrophilic portions of the polymer dissolve in solution and help stabilize the nanostructures. In one embodiment, an amphiphilic polymer includes, but is not limited to:

an amphiphilic multiblock copolymer, such as a diblock copolymer or a triblock copolymer,
an amphiphilic random copolymer,
an amphiphilic alternating copolymer,
an amphiphilic copolymer consisting of hydrocarbons and maleic anhydride groups; and
an amphiphilic polymer of the general formula (I):

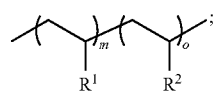

an amphiphilic polymer of the general formula (II):

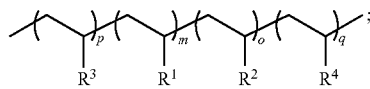

or an amphiphilic polymer of the general formula (III):

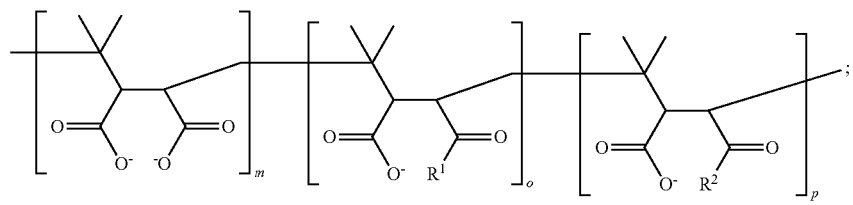

wherein each of m, o, p and q is an independently selected integer from about 3 to about 400, $R^1$ is a first hydrophilic moiety with about 0 to about 20 carbon atoms and 0 to about 3 heteroatoms selected from the group N, O, S, Se and Si, and $R^2$ is a first hydrophobic moiety with about 0 to about 20 carbon atoms and 0 to about 3 heteroatoms selected from the group N, O, S, Se and Si, and $R^3$ and $R^4$ may independently be selected from a hydrophilic or hydrophobic moiety and may be same as $R^1$ or $R^2$, with about 3 to about 80 carbon atoms and 0 to about 40 heteroatoms selected from N and O, S, Se and Si, wherein one or more of $R^1$, $R^2$, $R^3$ and $R^4$ may independently be a copolymerisable group; or mixtures of the aforementioned amphiphilic polymers.

The term "amphiphilic" as used herein refers to a polymer that has at least two portions or two types of functional groups; one is soluble in polar solvent (hydrophilic portion or moiety) and the other in a non-polar solvent (hydrophobic portion or moiety). It also encompasses multiphase polymers albeit an amphiphilic polymer described herein can be used also in only one phase and may be employed to solubilise matter in a desired phase, including stabilizing a phase interface and for phase-transfer purposes. The amphiphilic properties of the polymer are due to the presence of both polar (hydrophilic) and non-polar (hydrophobic) moieties within the same polymer. In this regard the polymer may be of surfactant nature. Accordingly, the polar properties of a polymer according to the invention are based on polar moieties. One such moiety is a —COOH side group, in particular in the form of a charged COO⁻ groups, that the hydrocarbon backbone of the polymer carries. Hydrophilic moieties refer to ionic groups or groups that form hydrogen bonding with water, such as —OH, —NH$_2$, —C═O, —COOH, to name only a few. Generally, a surfactant molecule includes a polar (hydrophilic) headgroup attached to a non-polar (hydrophobic) moiety. Non-polar or hydrophobic moieties of the polymer include the hydrocarbon backbone as well as aliphatic, alicyclic, aromatic and/or arylaliphatic moieties that the hydrocarbon backbone carries. Thus, the amphiphilic polymer encapsulation layer comprises a plurality of amphiphilic polymers with each amphiphilic polymer having a hydrophobic end for interacting with the metal particle and a hydrophilic end for interacting with an aqueous medium.

In the example of an amphiphilic polymer shown in formula (I) each of m, o, p and q is an independently selected integer from 0 to about 400, including from 1 to about 400 or about 2 to about 400, such as about 0 to about 400, about 0 to about 350, about 0 to about 300, about 3 to about 300, about 0 to about 250, about 0 to about 200, about 2 to about 200, about 0 to about 150, about 2 to about 150, about 0 to about 200, about 1 to about 200, about 3 to about 100, about 2 to about 100, about 0 to about 100, about 3 to about 50, about 2 to about 50, about 1 to about 50 or about 0 to about 50. As further illustrations, m may in some embodiments be selected in the range from about 5 to about 50, such as about 10 to about 45 including about 10 to about 43, whereas p may for instance be selected in the range from about 3 to about 40, such as about 3 to about 35 or about 4 to about 30, p may for example be selected in the range from 0 to about 30, such as from 0 to about 25 or from 0 to about 20, and q may for example be selected in the range from 0 to about 30, such as from 0 to about 25 or from 0 to about 20. The sum of m+o is selected in the range from about 6 to about 800, including about 6 to about 700, about 6 to about 600, about 6 to about 500, about 6 to about 400, about 6 to about 300, about 6 to 200, about 6 to about 100, about 6 to about 75, about 6 to about 60, about 6 to about 40, about 6 to about 25, about 6 to about 15, about 6 to about 10. The sum of (m+o+p) is selected in the range from about 9 to about 1200, including about 9 to about 1100, about 9 to about 1000, about 9 to about 900, about 9 to about 800, about 9 to about 700, about 9 to about 600, about 9 to about 500, about 9 to about 600, about 9 to about 500, about 9 to about 400, about 9 to about 300, about 9 to about 200, about 9 to about 100, about 9 to about 50, about 15 to about 40, or about 20 to about 30. The sum of (m+o+p+q) is selected in the range from about 12 to about 1600, including about 12 to about 1400, about 12 to about 1200, about 12 to about 1100, about 12 to about 1000, about 12 to about 900, about 12 to about 800, about 12 to about 700, about 12 to about 600, about 12 to about 400, about 12 to about 250, about 12 to about 150, about 12 to about 100, about 15 to about 150, about 20 to about 150, about 15 to about 100, or about 20 to about 100.

In some embodiments each of m, o, p and q is an independently selected integer from about 2 to about 300, including from about 3 to about 300, about 3 to about 250, about 3 to about 200, about 3 to about 150 or about 2 to about 200, about 3 to about 100, about 2 to about 100, about 3 to about 80, about 2 to about 80, about 3 to about 40 or about 2 to about 40

It is understood that the individual units indicated in formulas (I), (II) and (III) may be arranged in any, including random, order—rather than in the form of blocks. Thus, general formulas (I) and (II) merely define that
m units of:

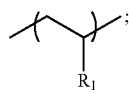

o units of:

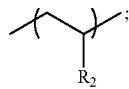

p units of:

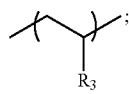

and q units of:

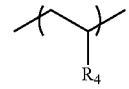

are present in the polymer, whereas general formula (III) merely defines that
m units of:

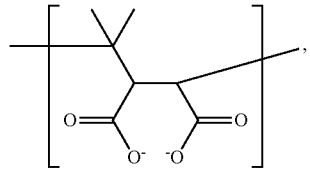

o units of:

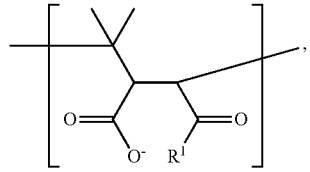

and p units of:

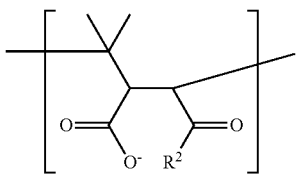

are present in the polymer. An amphiphilic polymer may therefore encompass any sequence of these units. As an illustrative example of a polymer according to general formula (III) a respective sequence may include the following arrangement of units:

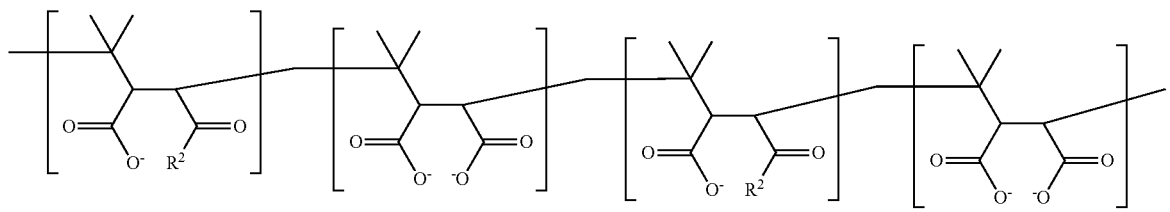

Such an amphiphilic polymer may be prepared by a process as described in WO 2009/038544 A1. The amphiphilic polymer is typically at least essentially free of cross-links. Accordingly, in the amphiphilic polymer the copolymerisable group (supra) of the first hydrophobic moiety $R^2$ is available for any crosslinking or copolymerization reaction.

With respect to the amphiphilic polymer, the term "aliphatic" means, unless otherwise stated, a straight or branched hydrocarbon chain, which may be saturated or mono- or poly-unsaturated and include heteroatoms (see below). An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

With respect to the amphiphilic polymer, the term "alicyclic" means, unless otherwise stated, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties which that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted. Examples of such moieties include, but are not limited to, cyclohexenyl, cyclooctenyl or cyclodecenyl.

With respect to the amphiphilic polymer, the term "aromatic" means, unless otherwise stated, a planar cyclic hydrocarbon moiety of conjugated double bonds, which may be a single ring or include multiple fused or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cylcopentadienyl, phenyl, naphthalenyl-, anthracenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl-, naphthaquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-(azacyclodecapentaenyl-), diazecinyl-, azacyclododeca-1,3,5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

With respect to the amphiphilic polymer, the term "arylaliphatic" means a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties such as alkylaryl moieties include, but are not limited to, 1-ethyl-naphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethylphenyl)ethyl]-4-ethyl-quinazoline or, 7,8-dibutyl-5,6-diethyl-isoquinoline.

Each of the terms "aliphatic", "alicyclic", "aromatic" and "arylaliphatic" as used herein in connection with the amphiphilic polymer is meant to include both substituted and unsubstituted forms of the respective moiety. Substituents may be any functional group, as for example, but not limited to, amino, amino, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methane-sulfonyl.

The aliphatic moieties, which the hydrocarbon backbone carries, may carry further moieties such as side chains. Such further moieties may be an aliphatic, alicyclic, aromatic, arylaliphatic or arylalicyclic group that typically is of a main chain length of 1 to about 10, to about 15 or to about 20 carbon atoms. These further moieties may also carry functional groups (supra).

The hydrocarbon backbone can carry one or more aliphatic groups, such as first and second aliphatic moieties or more. In one embodiment two aliphatic moieties are present, the first aliphatic moieties have a main chain of about 3 to about 20 carbon atoms, including about 5 to about 20 carbon atoms, about 7 to about 20 carbon atoms, such as 3, 4, 5, 6, 7, 8, 9, 10, 11, 12, 13, 14, 15, 16, 17, 18, 19 or 20 carbon atoms or about 5 to about 15 carbon atoms. Further, the first aliphatic moieties have 0 to about 3 heteroatoms, including 1, 2 or 3 heteroatoms, such as N, O, S, Se or Si. An illustrative example of a suitable first aliphatic moiety is an alkyl moiety with a heteroatom, via which it is bonded to a carbonyl group carried by the aliphatic backbone of the polymer. Instead of a free carboxyl group the backbone thus carries an ester, a thio ester, a seleno ester or an amido group. In one embodiment the first aliphatic moiety is linked to the backbone via an amide bond which is formed by reacting the respective amine with the maleic anhydride polymer and is defined by an unbranched alkyl moiety, such as an n-octyl moiety.

The second aliphatic moieties have a main chain of about 3 to about 80 carbon atoms, including of about 3 to about 60 carbon atoms, of about 3 to about 40 carbon atoms, of about 10 to about 80 carbon atoms, of about 10 to about 60 carbon atoms, of about 25 to about 60 carbon atoms, of about 10 to about 40 carbon atoms, of about 3 to about 20 carbon atoms or about 3 to about 10 carbon atoms, such as 3, 4, 5, 6, 7, 8, 9, 10, 11, 12, 13, 14, 15, 16, 17, 18, 19, 20, 24, 25, 26, 27, 28, 29, 30, 31, 32, 33, 34, 35, 36, 37, 38, 39, 40, 41, 42, 43 or 44 carbon atoms. Further, the second aliphatic moieties have 0 to about 44 heteroatoms, including 0 to about 40 heteroatoms, 1 to about 40 heteroatoms, about 2 to about 40 heteroatoms, about 2 to about 30 heteroatoms or about 0 to about 3 heteroatoms such as 1, 2, 3, 4, 5, 6, 7, 8, 9, 10, 11, 12, 13, 14, 15, 16, 17, 18, 19, 20, 21, 22, 25, 26, 27, 28, 29, 30, 31, 32, 33, 34, 35, 36, 37, 38, 39, 40, 41, 42, 43 or 44 heteroatoms, such as N or O.

The amphiphilic polymer may further have one or more copolymerisable groups, as explained above. The copolymerisable group may also be called cross-polymerisable in order to emphasize that both intra- and intermolecular copolymerization can occur. The copolymerisable group is typically also cross-linkable. The copolymerizable group can be any group that bears functionality of monomer, i.e. any such desired group that can be polymerized. The usability of each group may depend on several conditions, for example the respective application, the reaction conditions, the wanted degree of water-solubility of the resulting polymer, etc and can be determined empirically, if wanted. Examples of a suitable copolymerisable group include, but are not limited to, an amino group, a hydroxyl group, an epoxide group, an oxetane group, a C=C group (either an internal C=C group and/or a terminal C=C group) such as an allyl group as well as an allyl glycidyl ether group, a C≡C group (either an internal C≡C group and/or a terminal C≡C group), a coupled —C=C—C=C— group (either an internal coupled —C=C—C=C— group and/or a terminal coupled —C=C—C=C— group) or substituted derivatives thereof. The copolymerisable group may be bonded to any position of the amphiphilic polymer, such as, for example, a second aliphatic moieties and can be an internal group and/or a terminal group. In some embodiments it is a terminal functional group, for example a terminal C=C group. As an illustrative example, the terminal C=C group may be a vinyl group such as —CH=CH$_2$. Examples of an internal C=C group further include, but are not limited to, an allyl group such as —CH=CH—CH$_3$ or an acryl group such as —CH=CH—C(O). The tem "internal" thus refers to a copolymerisable group in which the terminal main chain atom is not part of the copolymerisable reaction centre. Non limiting examples of suitable C=C groups, both internal and terminal, may be acrylic and methacrylic amides, acrylic and methacrylic esters, vinyl or acetylene moieties or a butadiene moiety.

In one embodiment, the second aliphatic moieties may be defined by a poly(ethylene oxide) including chain. The poly(ethylene oxide) including chain may for example include a polyethyleneglycol (PEG) or a diaminoalkyl-polyethyleneglycol moiety. The PEG may react with any suitable group on the hydrocarbon backbone to be linked thereto. For example, only one terminal group of the polyethyleneglycol or the diaminoalkyl-polyethyleneglycol is allowed to react with the maleic anhydride polymer of formula (III). PEG is commercially available over a wide range of molecular weights. The lower limit of molecular weight of the polymer may be higher than 100, depending on the size and number of groups present in each repeating unit. If the polymer is derived from a low molecular weight repeating unit (e.g. having small side chains) such as a polyol or a polyamine, then the lower limit of the molecular weight of the polymer can be low. In the case of a polymer in which the repeating units have a high molecular weight (e.g. bearing bulky side chains), then the lower limit may be higher than 100. In some embodiments, the lower limit of molecular weight of a polymer may be about 400, about 500, about 600, about 1000, about 1200, about 1500, or higher at about 2000. For example, the PEG may have a molecular weight of more than about 500, more than about 1000, more than about 5000, more than about 10000 or even more than about 25.000 daltons. The molecular weight can for example be chosen in such a way, that an efficient wrapping of the amphiphilic polymer around a metal particle is or can be ensured. PEG is known to increase the colloidal stability of particles. Further, PEGylated surfaces offer reduced nonspecific interaction with biological molecules and cells. The more PEG that is attached to the polymer shell, the bigger the size of the resulting particles. Illustrative examples of a suitable polyethyleneglycol moiety are a (methoxypoly(ethylene glycol)), abbreviated mPEG, or PEG 600 moiety. Numerous PEG are available having different geometries. An illustrative example of a suitable diaminoalkyl-polyethyleneglycol moiety is a diaminopropyl PEG moiety. The diaminoalkyl-polyethyleneglycol moiety may for instance be PEG(NH$_2$)$_2$ 1500 or a PEG (having one or two amino groups) with an molecular weight of about 5000 to 6000. In the meantime the ease of the formation of such polymers has been confirmed by the synthesis of a polymer in which the first aliphatic moiety is a dodecylamino moiety.

In a further embodiment, the second aliphatic moieties may be chosen from further polymers that may be water soluble. For example, polymers having a terminated nucleophilic function may be used. Examples of such polymers are, but are not limited to, polypropylene glycol, polyacrylic acid, polystyrene sulfate, polylactic acid or polyvinyl alcohol. Further polymers known to the skilled man in the art having comparable properties may also be used.

In another embodiment an amphiphilic copolymer consisting of hydrocarbons and maleic anhydride groups can be used. Examples of such polymers include, but are not limited to poly(maleic anhydride-octadecene) (PMAO).

The amphiphilic random copolymer can include, but is not limited to random copolymer poly(methyl acrylate-co-acrylic acid); random copolymer poly(methyl methacrylate-co-n-butyl acrylate); random copolymer poly(methyl methacrylate-co-hydroxypropyl acrylate); random copolymer poly(styrene-co-p-carboxyl chloro styrene); random copolymer poly(styrene-co-4-hydroxystyrene); random copolymer poly(styrene-co-4-vinyl benzoic acid); random copolymer poly(styrene-co-4-vinyl pyridine), and combinations thereof.

The amphiphilic alternating copolymer can include, but is not limited to, poly(maleic anhydride-alt-1-octadecene), poly(maleic anhydride-alt-1-tetradecene), alternating copolymer poly(carbo tert.butoxy α-methyl styrene-alt-maleic anhydride) and alternating copolymer poly(carbo tert.butoxy norbornene-alt-maleic anhydride), and combinations thereof.

In another embodiment, an amphiphilic multiblock copolymer, such as a diblock (A-B) or an amphiphilic triblock copolymer (A-B-A or A-B-C) can be used as amphiphilic polymer. A polyether comprised in such diblock (A-B) or triblock copolymers (A-B-A or A-B-C) may for example include one of a poly(methyl methacrylate) block, a poly (lactide) block, a poly(caprolactone) block, a poly(2-methyloxazoline) block, a poly(ethylene glycol) block, a poly (dimethylsiloxane) block, an oligo(oxyethylene) block or segment, a poly(oxyethylene) block (or segment), an oligo (oxypropylene) block, a poly(oxypropylene) block, a polystyrene block, an oligo(oxybutylene) block or a poly(oxybutylene) block.

An illustrative example of a respective amphiphilic triblock copolymer is a poloaxamer. A poloaxamer is a difunctional block copolymer surfactant terminating at the hydrophilic end in primary hydroxy groups. The lengths of the polymer blocks can be customized, so that a large variety of different amphiphilic poloxamers with slightly different properties is commercially available. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic trade name, coding of these copolymers starts with a letter to define it's physical form at room temperature (L=liquid, P=paste, F=flake (solid)) followed by two or three digits, the first digit(s) refer to the molecular mass of the polyoxypropylene core (determined from BASF's Pluronic grid) and the last digit×10 gives the percentage polyoxyethylene content (e.g., F127=Pluronic with a polyoxypropylene molecular mass of 4,000 g/mol and a 70% polyoxyethylene content). The polyether may for example be a triblock copolymer of oxirane with 2-methyl-oxirane, having the Chemical Abstract No. 691397-13-4. Illustrative examples of such a polyether are the commercially available triblock copolymers P188 and P407.

Further examples of amphiphilic triblock copolymers include, but are not limited to poly(ethylene oxide)-block-poly(dimethyl)siloxane-block-poly(2-methyl oxazoline) (PEO-b-PDMS-b-PMOXA), polystyrene-block-poly (methyl methacrylate)-block-poly(acrylic acid), such as (PS$_{180}$-b-PMMA$_{67}$-b-PAA$_{37}$), poly(5-(N,N-dimethylamino) isoprene)-block-polystyrene-block-poly(methacrylic acid)), poly(acrylic acid)-block-polystyrene-poly(4-vinyl pyridine), methoxy-poly(ethylene glycol)-block-poly(L-lactide)-block-poly(L-lysine) or mixtures thereof.

Examples of diblock copolymers include, but are not limited to poly(acrylic acid-block-methyl methacrylate), poly(methyl methacrylate-block-sodium acrylate), poly(t-butyl methacrylate-block-ethylene oxide), poly(methyl methacrylate-block-sodium methacrylate), poly (methyl methacrylate-block-N-methyl 1-4vinyl pyridinium iodide), poly(methyl methacrylate-block-N,N-dimethyl acrylamide), poly(butadiene-block-methacrylate acid and sodium salt), poly(butadiene(1,2 addition)-block-acrylic acid), poly(butadiene(1,2 addition)-block-sodium acrylate), poly(butadiene (1,4 addition)-block-acrylic acid), poly(butadiene(1,4 addition)-block-sodium acrylate), poly(butadiene(1,4 addition)-block-ethylene oxide), poly(butadiene(1,2 addition)-block-ethylene oxide), poly(styrene-block-acrylic acid), poly (styrene-block-acrylamide), poly(styrene-block-cesium acrylate), poly(styrene-block-sodium acrylate), poly(styrene-block-ethylene oxide), poly(styrene-block-methacrylic acid), poly(styrene-block-sodium methacrylate) or mixtures thereof.

In one embodiment, the diblock copolymer and the triblock copolymer are selected to comprise a hydrophilic chain of monomeric units and a hydrophobic chain of monomeric units, wherein the number of monomeric units in the hydrophilic chain is higher than the number of monomeric units in the hydrophobic chain. It was demonstrated for certain molecules that a longer hydrophilic chain in an amphiphilic diblock copolymer can enhance the stability of the Raman active composite material.

Therefore, in one embodiment, the number of monomeric units in the hydrophilic chain is between about 10 to about 1000, or between about 10 to about 500, or between about 50 to about 500, or between about 50 to about 750, or between about 100 to about 500, or between about 120 to about 250. The number of monomeric units in the hydrophobic chain can be between about 30 to about 1000, or between about 30 to about 500, or between about 50 to about 500, or between about 50 to about 750, or between about 100 to about 750, or between about 100 to about 500, or between about 60 to about 250. In one example a PS-PAA diblock polymer is used wherein the number of the hydrophilic monomeric units of PS is 154 while the number of the hydrophobic monmeric units of PAA is 60 (written PS$_{154}$PAA$_{60}$ or PS$_{154}$-block-PAA$_{60}$). Other examples include, but are not limited to PS$_{154}$PAA$_{60}$, PS$_{144}$PAA$_{28}$, PS$_{404}$PAA$_{62}$, PS$_{108}$PGA$_{108}$, and PS$_{132}$PAA$_{72}$.

In the present invention polydisperse as well as monodisperse amphiphilic polymers can be used. The dispersity is indicated by the polydispersity index ($M_w/M_n$ molecular weight distribution). In a monodisperse amphiphilic polymer the index would be 1 while in a polydisperse system the index would be different from 1. The smaller the number the more uniform the chain lengths. In another embodiment, the molecular weight distribution ($M_w/M_n$) of the amphiphilic polymer can be between about 1 to about 20, or between about 1 to 15, or between about 1 to 12, or between about 1 to 10, or between about 1 to 8, or between about 1 to 5, or between about 1 to 4, or between about 1 to 2.

Even though not necessary, it is possible to enhance the coating around metal particle which is coated with the Raman active molecule. Therefore, in one embodiment, adjacent amphiphilic polymers can be linked together by a bridging molecule so that the amphiphilic polymers are linked together to form a cohesive encapsulation around the metal particle that will not dissociate in water over long periods of time and that can provide a strong and stable anchorage for a recognition moiety that may be attached to the hydrophilic ends of the amphiphilic polymers.

Bridging molecules can be multidentate bridging molecules having one or more reactive functional groups that can react with and bond to one or more hydrophilic functional groups of a hydrophilic end of an adjacent amphiphilic polymer thereby crosslinking adjacent amphiphilic polymers together. Therefore, the self-assembled amphiphilic polymer encapsulation is knit together to form a cohesive encapsulation around the metal particle which is coated with the Raman active molecule that will not dissociate in water over long periods.

The multidentate bridging molecule can comprise one or more than one type of reactive functional group. Examples of such reactive functional groups include, but are not limited to hydroxy (OH), carboxylate (COOH), amine ($NH_2$) groups, and any combinations thereof. In one embodiment, a bridging molecule is diamine, 2,2'-(ethylenedioxy)bis(ethylamine) and the amine functional groups on the diamine react with hydrophilic functional groups that are carboxylate groups on a hydrophilic end of an amphiphilic polymer to form a stable peptide bond.

In principal all kinds of metals or metal alloys can be used for the metal particles referred to herein. In one embodiment, the metal particle referred to herein can be selected from the group including metallic ferromagnetic particles, metallic paramagnetic particles and a noble metal particle.

The metal particle can include noble metal particles made of silver, gold, palladium, platinum, ruthenium, rhodium, osmium, iridium and alloys of the aforementioned materials. In one embodiment gold or silver particles are used.

Metallic ferromagnetic particles can also be used. Metallic ferromagnetic materials have a large and positive susceptibility to an external magnetic field. They exhibit a strong attraction to magnetic fields and are able to retain their magnetic properties after the external field has been removed. Examples of metallic ferromagnetic particles include, but are not limited to particles of any one of the following materials: Fe, FePt, FePd, MnBi, Ni, MnSb, MnAs, MnAl, Gd, Dy, Co, CoPt, $Co_3Pt$, CoPtCr, $Fe_{14}Nd_2B$, $SmCo_5$ and alloys of the aforementioned materials.

Metallic paramagnetic particles can also be used. Metallic paramagnetic materials have a small and positive susceptibility to magnetic fields. These materials are slightly attracted by a magnetic field and the material does not retain the magnetic properties when the external field is removed. Examples of ferromagnetic particles include, but are not limited to particles of any one of the following materials: Mg, Mo, Li, Ta and alloys of the aforementioned materials.

The metal particle used can be of any shape. For example, the metal particle can be a nanosphere, a nanocube, a nanorod, a nanotube or a nanowire. The encapsulation layer can encapsulate one single metal particle or a plurality of metal particles. For example, the encapsulation layer can encapsulate 2, 3, 4, 5, 6, 7, 8 or even more metal particle at once, i.e. it forms a continuous layer around all these metal particles.

Figure 8:
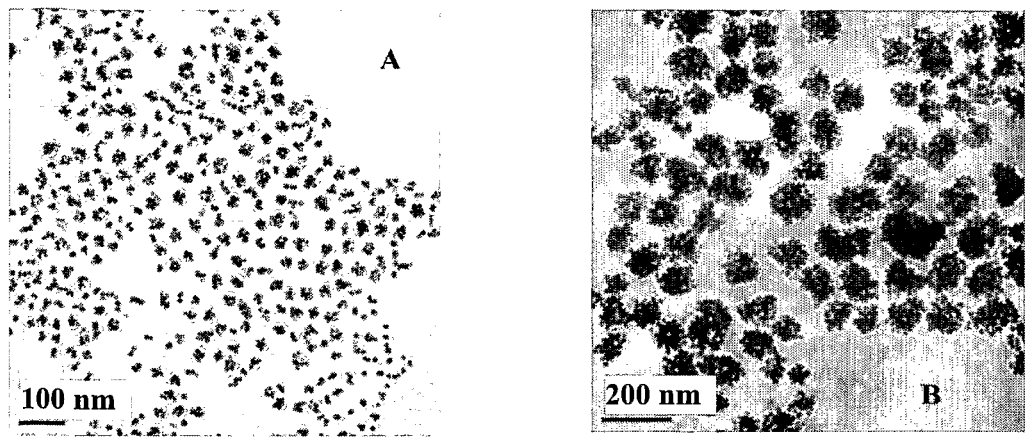
FIG. 8 shows TEM images of Au nanoparticle aggregates having different aggregation sizes. The Au nanoparticles are coated with a first layer of 4-ethylbenzenethiol and encapsulated with $PS_{154}$-block-$PAA_{60}$. The size of the NP aggregates size was changed by adjusting the acid concentration. (0.06 mM of acid for FIG. 8A and 0.12 mM of acid for FIG. 8B).
Figure 10:
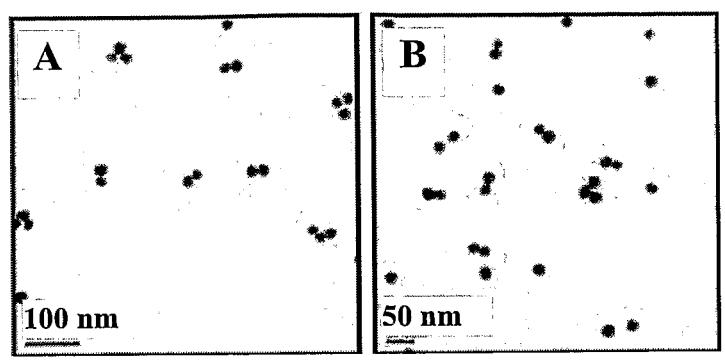
FIG. 10 shows TEM images of anisotropically encapsulated Raman reporter coated metal nanoparticles.
Figure 10:
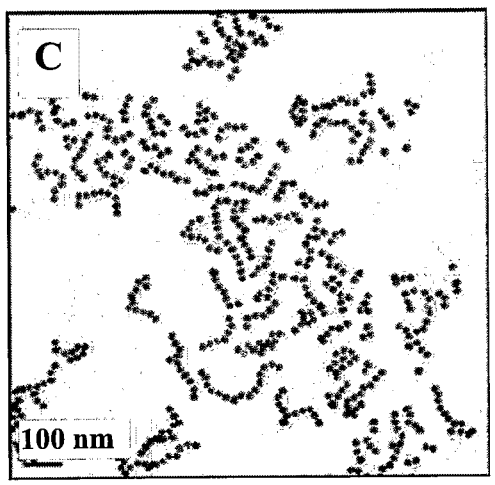

In one embodiment, the Raman active composite material comprises aggregates of metal particles which are encapsulated in one continuous layer of amphiphilic polymers as illustrated for example in FIGS. 8 and 10C. Aggregates refer to clusters of at least two metal particles which are encapsulated by a shell of amphiphilic polymers. The particle aggregates have stronger SERS intensity compared to single particle probe of a same size. This is due to the strong plasmonic coupling between the neighbouring particles. Those aggregates are either encapsulated in a shell of amphiphilic polymers of uniform thickness or they are encapsulated in an anisotropic manner, i.e. the encapsulation is not uniform but can be interrupted by short sections which are not encapsulated with an amphiphilic polymer thus providing the opportunity for further modification of the Raman active composite material described herein.

Depending on the application, the metal nanoparticles used are microparticles or nanoparticles. While nanoparticles are preferred for labelling of small biomolecules, larger micron-sized particles, or collection of nanoparticles of micron size are preferred for other applications, such as the labelling of cells. Thus, in one embodiment, at least one dimension of the metal particle is in the micrometer range, i.e. is a microparticle. A microparticle can have a size at least in one dimension of between about 1 µm to about 200 µm, or between about 1 µm to about 150 µm, or between about 1 µm to about 100 µm, or between about 1 µm to about 50 µm, or between about 1 µm to about 20 µm, or between about 1 µm to about 10 µm, or between about 1 µm to about 2, 3, 4, 5 or 6 µm. The lower end of the microparticle size of 1 µm can also be 2 µm, 3 µm, 5 µm, 10 µm or 20 µm. In case a spherical metal microparticle is used the above sizes refer to the diameter of the spherical metal microparticle.

In one embodiment at least one dimension of the metal particle is in the nanometer range, i.e. is a nanoparticle. A metal nanoparticle can have a size at least in one dimension of between about 5 nm to about 900 nm, or between about 5 nm to about 500 nm, or between about 5 nm to about 300 nm, or between about 5 nm to about 100 nm, or between about 5 nm to about 50 nm, or between about 50 nm to about 200 nm. Instead of 5 nm the lower size end can also be 2 or 3 nm. In case spherical metal nanoparticles are used the above sizes refer to the diameter of the spherical metal nanoparticle.

In general, the coating layer of the at least one type of Raman active molecule as well as the encapsulation layer of the at least one type of amphiphilic forms a uniform layer around the metal particle. However, it is also possible that the encapsulation layer encapsulates the metal particle in an anisotropic manner. The term "anisotropic" as used herein describes a structure whose appearance varies with the angle of observation and whose surface functionalities differ from one position to another (not isotropic). In the present case that means that the metal particle which is coated with the covering layer of the Raman active molecule is not fully encapsulated with the encapsulation layer of the amphiphilic polymer.

Figure 9:
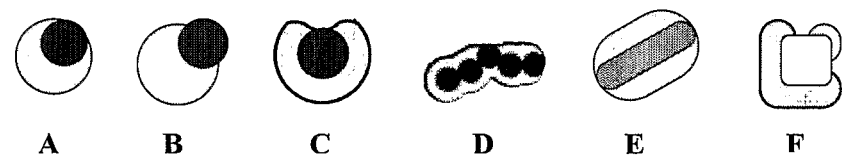
FIG. 9 shows non-limiting examples of anisotropically encapsulated metal nanoparticles which are coated with a Raman active molecule.
Figure 9:
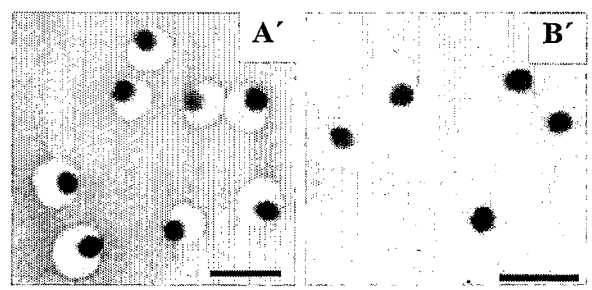

FIG. 9 shows some examples of possible configurations of anisotropically encapsulated metal nanoparticles which are coated with a Raman active molecule. In more detail, a metal nanoparticle encapsulated in a shell of an amphiphilic polymer in a homocentric manner refers to a metal nanoparticle which is encapsulated around its whole circumference in a uniform manner, i.e. the thickness of the amphiphilic polymer shell is the same around the whole metal nanoparticle. In contrast, the nanoparticles shown in FIG. 9 are encapsulated in an eccentric manner which means that a portion of the metal nanoparticle does not bind to an amphiphilic polymer. Such non-symmetrically encapsulated or anisotropic Raman active composite materials open up opportunities for tailored particle organizations and functionalization. The non encapsulated portion of a particle allows for example binding of further recognition moieties as defined herein or of linkers which are suitable to bind the Raman active composite material described herein to a solid support.

In another embodiment, the Raman active composite material further comprises a recognition moiety (binding ligand) which is bound to the amphiphilic polymer. The recognition moiety can be bound to the amphiphilic polymer either by covalent linkage (e.g., by amide bond, using —COOH groups from polymer and $NH_2$ groups from proteins/DNA), or static charge interactions. Techniques for coupling recognition moieties to reactive groups of an amphiphilic polymer are known in the art and comprise for example the coupling via N-(3-dimethylaminopropyl)-N'-ehtylcrbodiimide (EDC) chemistry.

A recognition moiety can be a nucleotide, a nucleic acid molecule, a peptide, a protein, a lipid, a carbohydrate, a drug, a drug precursor, a drug candidate molecule, a drug metabolite, a vitamin, a synthetic polymer, a receptor ligand or a metabolite. A recognition moiety may for instance have affinity for selected target matter. Examples of a respective ligand include, but are not limited to, an immunoglobulin, a fragment thereof, a domain antibody such as a diabody, a triabody or a decabody, or a proteinaceous binding molecule with antibody-like functions such as a mutein based on a polypeptide of the lipocalin family, a glubody, a protein based on the ankyrin scaffold or the crystalline scaffold, an AdNectin, a tetranectin, an avimers or a peptoid.

In another aspect, the present invention refers to a method of manufacturing a Raman active or enhanced Raman scattering composite material. The method can comprise in a first step the incubation of a metal particle with a Raman active molecule and an organic solvent in a first solution. The time for the incubation step is selected to be sufficient to allow self-assembly of the Raman active molecules to coat the metal particle. Afterwards an amphiphilic polymer is added to the first solution which comprises the metal particles now coated with the Raman active molecule. After addition of the amphiphilic polymer to the first solution, the first solution is incubated for a time sufficient to allow self-assembly of an amphiphilic polymer shell around the metal particle. At the end the first solution obtained by addition of the amphiphilic polymer is cooled. This method allows obtaining a product in which almost all (about 99%) of the metal particles are encapsulated separately, i.e. single encapsulation of metal particles.

In another embodiment, the step of incubating the first solution after adding the amphiphilic polymer for a time sufficient to allow self-assembly of an amphiphilic polymer shell around the metal particle includes heating the first solution after adding the amphiphilic polymer. One advantage of this method is that in the cooling phase the critical concentration for forming the encapsulation layer slowly decreases with temperature which leads to the exclusion of the amphiphilic polymer and self-assembly into an encapsulation layer which forms around the metal particle which is already covered with the coating layer of the Raman active molecule. FIG. 3 shows TEM images of samples of different Raman active composite materials formed with this method around metal particles of different shape covered with Raman active molecules. Measurements revealed that the uniform thickness of the encapsulation layer formed is consistent with a thermodynamically controlled self-assembly process.

In previous reports that prepared silica-coated, analyte-tagged nanoparticles, two competing ligands have to be used for binding to the metal nanoparticle surface: a SERS-active reporter and a vitreophilic coupling agent such as APTMS (Mulvaney, S. P., Musick, M. D., et al., 2003, supra). In contrast, only one Raman active molecule was used in the preparation method described herein to fully cover the surface of metal particles. In addition to accommodating more reporter molecules per metal particle, the present design avoids the problem of the mutually exclusive ligand binding competition that likely results in uneven loading of reporter molecules on individual metal particles. In this system, the ensemble-averaged SERS signature (that means the Raman spectrum measured from a collection of such Raman active composite particles) is a close representation for the individual metal particles, considering that (a) a single ligand covers uniformly on the surface of the metal particle; (b) all metal particle have a well-defined core/shell structure with uniform shell thickness; and in preferred embodiments (c) each amphiphilic polymer encapsulation layer contains only one metal particle.

Ensemble-averaged SERS signals from the Raman active composite material were characterized by solution Raman spectroscopy. In the particular case of using 2-naphthalenethiol as reporter, the signals are consistent with reported values in the literature (Alvarez-Puebla, R. A., Dos Santos, D. S., et al., 2004, Analyst, vol. 129, pp. 1251). No extra peak was observed that could be assigned to the SERS of a component of the amphiphilic polymer, suggesting that the surface of the metal particle was covered by the Raman active molecule.

The organic solvent used to dissolve the metal particle and the Raman active molecule can be a polar solvent or a polar aprotic solvent that is miscible with water. Examples for a polar solvent include, but are not limited to dimethylformamide (DMF), dimethyl sulfoxide, dioxane and hexamethylphosphorotriamide, tetrahydrofuran and mixtures thereof.

The step of incubating the metal particle with the Raman active molecule and the organic solvent can be carried out at a temperature between about 0° C. to about 100° C. or between about 30° C. to about 100° C., or between about 30° C. to about 80° C., or between about 50° C. to about 80° C., or at about 30, 40, 50, 60, 70, 80, 90, 100° C. The lower the temperature the longer the reaction time for the coating of the metal particle with the Raman active molecule. After heating of the mixture of metal particle, Raman active molecule and organic solvent the mixture or solution is left to cool down. In one embodiment, the mixture is left to cool down to room temperature (i.e. about 25° C.). In this phase the Raman active molecule binds via its functional groups (amine, thiol, etc.) to the surface of the metal particle.

The amphiphilic polymer, which is to be added to the first solution comprising the metal nanoparticle now coated with the Raman active molecule, can be dissolved in a suitable organic solvent, such as a polar solvent or a polar aprotic solvent that is miscible with water before being added to the solution of the metal particle, the Raman active molecule and the organic solvent. After adding the amphiphilic polymer to the solution of the metal particle, the Raman active molecule and the organic solvent, water can be added to the solution. The organic solvent to water ratio should be high enough to prevent the aggregation of particles and low enough for the concentration of amphiphilic polymer to be below its critical micelle concentration. Thus, in one embodiment the method comprises the step of adding water to the first solution comprising the Raman reporter molecule coated metal particle and the amphiphilic polymer. The organic solvent to water ratio in the reaction mixture (i.e. the first solution) depends on the organic solvent used but can generally be between about 1:0.1 to about 10:1. In one embodiment, DMF is used as organic solvent and the ratio of DMF to water can be, for example, between about 1:1 to about 3:1 or about 4.5:1, or about 8:1. In another embodiment tetrahydrofuran (THF) is used as organic solvent. The THF to water ratio in the reaction mixture can be between about 1:2 to about 8:1. In one embodiment, the ratio is about 1:2 or about 3:1, or about 8:1.

After mixing the amphiphilic polymer into the solution with the metal particle, the solution is incubated at a temperature of between about 0° C. to about 200° C. or between about 0° to about 150° C. or between about 10° C. to about 150° C., or between about 15° C. to about 150° C. The purpose of this incubation is to allow sufficient time for the polymer to self-assemble on/near the metal particles. Generally speaking, higher temperature speeds up this process. In one embodiment the solution is heated. Heating of the solution can be carried out at a temperature of between about 60° C. to about 200° C., or between about 80° C. to about 200° C., or between about 60° C. to about 150° C., or between about 80° C. to about 150° C.

The incubation can be carried out for a time between about 1 min to about 7 h, or between about 10 min to about 7 h, or between about 30 min to about 5 h, or between about 50 min to about 5 h, or between about 10 min to 2 h, or between about 30 min to 2 h, or between about 50 min to 2 h, or between about 2 to about 5 h, or between about 2 to about 4 h, or between about 2 to about 3 h or for about 1, 1.5, 2, 2.5, 3, 3.5, 4, or 5 h. In case the solution is heated to a temperature above room temperature, the above incubation time starts to count from the time the solution is immersed in the oil bath with pre-set temperature, i.e. the solution can be kept at the elevated temperature for the time indicated in this paragraph.

After incubating or heating the solution for the time indicated above, it was left to be cooled down to room temperature to initiate the formation of the encapsulation layer through self-assembly of the amphiphilic polymer. In case the incubation has been carried out at a temperature below room temperature, cooling means to cool the solution below room temperature. For example, in case the incubation has been carried out at a temperature around 0° C., cooling means to cool the solution to below 0° C., such as −10° C. In general, heating of the solution for initiation of the formation of the encapsulation layer is required for a low organic solvent/water ratio but not in case of higher organic solvent/water ratios. For example, at an organic solvent/water ratio of 8:1 the encapsulation can already occur at room temperature, without the need for heating or cooling.

In one embodiment, more than one metal particle is to be encapsulated in a layer of amphiphilic polymer as shown for example in FIG. 8. To ensure that the above method leads to the encapsulation of more than one metal particle by one single encapsulation layer of amphiphilic polymer additional steps can be inserted into the method referred to above. In general, metal particles are stable in solution as long as the Raman active molecule at their surface is solubilized in solution and/or they carry surface charges and repel each other. The particles will aggregate when these factors are disrupted by these additional steps.

Thus, in one embodiment between the steps of incubating a metal particle with a Raman active molecule and an organic solvent in a first solution and the step of adding an amphiphilic polymer to the first solution, the following steps are inserted: inducing metal particle aggregation in the first solution by subjecting the first solution to a process which can include, but is not limited to adding water, acidifying the solution, basifying the solution, adding a salt to the solution, adding large excess of the Raman active molecule, heating the solution or a combination of the aforementioned processes. These processes of inducing aggregation can also be used for methods manufacturing anisotropically encapsulated Raman active composite materials. Adding large excess of Raman active molecule means to add at least 0.25 fold, 0.5 fold, 1.1 fold, 1.2 fold or 1.5 fold the amount of Raman active molecule already comprised in the first solution. In another embodiment the amount of Raman active molecule is doubled. In a further embodiment, the amount of the Raman active molecule is at least 2.5 fold, 3 fold, 3.5 fold or 4 fold the amount of Raman active molecule already comprised in the first solution.

After aggregation, the pH of the solution can be neutralized in case the solution was acidified or basified to induce aggregation.

Suitable salts that can be used for the above process include any inorganic salts. Any salt could increase the ionic strength of the reaction mixture, shielding the charge repulsion between the particles, and lead to aggregation. Examples, of inorganic salts include, but are not limited to $NaCl$, $KCl$, $CaCl_2$, $BaCl_2$, $MgCl_2$, $NaBr$, $KBr$, $NaI$, $KBr$, $NaNO_3$, $KNO_3$, $Mg(NO_3)_2$, $Ca(NO_3)_2$, $Na_2SO_4$, $K_2SO_4$, $NaClO_4$, $NH_4Cl$, $NH_4NO_3$, $(NH_4)_2SO_4$, $CH_3COONa$, $CH_3COONH_4$.

Examples for suitable bases which can be used for basifying can include, but are not limited to $NaOH$, $NH_3$, $KOH$, $Ba(OH)_2$, $CsOH$, $Sr(OH)_2$, $Ca(OH)_2$, $LiOH$, $RbOH$ and $Mg(OH)_2$. The pH can be between about 8 to 14 or between about 8 to 10 or between about 8 to 9 or between about 10 to 12 or between about 12 to 14 or about 8, 9, 10, 11, 12, 13, or 14.

The organic solvent used in the first mixture can be a polar or hydrophilic solvent. Examples for such solvents include any of the aforementioned organic solvents. Examples of organic solvents include, but are not limited to dimethylformamide (DMF), dimethyl sulfoxide, dioxane and hexamethylphosphorotriamide, tetrahydrofuran (THF) and mixtures thereof.

Any acid can be used for the process of acidifying to induce aggregation. Exemplary acids which can be used include, but are not limited to $HCl$, $HNO_3$, $H_2SO_4$, $HClO_4$, $HBr$, $HCOOH$ or $CH_3COOH$. The pH of the third mixture before mixing it with the second mixture can be between about 2 to 5 or between about 2 to 4 or between about 2 to 3 or about 2, 3, 4 or 5.

To control the size of the aggregates using an acid or a base the amount of acid or base used can be selected to be in the range of between about 1 mM to about 1M or between about 1 mM to about 100 mM or between about 10 mM to about 1 M or between about 0.01 mM to 1 mM or between about 0.01 to about 0.5 mM, or between about 0.01 to about 0.3 mM, or between about 0.01 to about 0.2 mM. The lower end of 0.01 can also be about 0.02 or about 0.03. For example, a concentration of the acid of about 0.06 mM leads to a size of the aggregates of about 16 nm (see FIG. 8A) while a concentration of about 0.12 mM leads to a size of the aggregates of about 130 nm) (see FIG. 8B). Encapsulated metal particle aggregates can be used to increase the SERS signal because the larger the metal particle or aggregates of metal particles, the stronger SERS signals. These bulky clusters could be used to label cells or collection of cells as opposed to biomolecules. Or they could be used to non-biological applications, for example for labelling and tracking of a piece of plastic of a cell phone.

When heating the solution to induce metal particle aggregation the temperature can be between about 30° C. to about 100° C. or between about 40° C. to about 100° C., or between about 50° C. to about 80° C. or at about 30, 40, 50, 60, 70, 80, 90, 100° C. Heating of the solution can be carried out for a time of between about 1 h to about 5 h, or between about 1 h to about 3 h, or between about 1 h to about 2 h or for about 1, 2, 3, 4 or 5 h.

Afterwards the amphiphilic polymer is added to the solution to proceed with the method as described above with the difference that the encapsulation layer forming through self-assembly is now encapsulating the metal-particle aggregates.

Isolation of the Raman active composite material thus formed can be carried out by any method known in the art. For example, the Raman active composite material can be isolated by direct centrifugation. After synthesis of the Raman active composite material the solution can be diluted in water to trap the Raman active composite material in a kinetically stable state. The organic solvent can be removed by repeated washing and centrifugation of the solution. Surprisingly, the Raman active composite material formed does not aggregate during these purification steps which suggests an extraordinary stability of the Raman active composite material.

In another aspect, the present invention refers to a method of manufacturing a Raman active composite material in which the metal particles are anisotropically encapsulated, wherein the method comprises:
providing a solution comprising a metal particle, an organic solvent, an amphiphilic polymer, a ligand comprising a binding moiety for binding to the metal particle and a Raman active molecule;
incubating the solution for a time sufficient to allow self-assembly of an amphiphilic polymer shell around the metal particle; and
cooling the solution.

This methods results in the manufacture of anisotropically encapsulated metal particles. Examples of such nonsymmetrical encapsulated metal particles are illustrated in FIG. 9.

The organic solvent used herein is the same as described above. Incubation of the solution for a time sufficient to allow self-assembly of an amphiphilic polymer shell around the metal particle is also carried out as already described above.

The ligand comprising a binding moiety for binding to the metal particle can be a hydrophilic or non-hydrophobic ligand, so that the hydrophobic section of the amphiphilic polymer would not attach to the surface functionalized by these ligands. The binding moiety can be any chemical group capable of binding to the metal surface of the metal particle. Examples of such binding moieties include, but are not limited to, thiols, amines, phosphines, phosphine oxides, and any combination thereof. The binding moieties can be bound to a polar or aliphatic group.

In connection with the ligand comprising a binding moiety bound to an aliphatic group, the term "aliphatic", alone or in combination, refers to a straight chain or branched chain hydrocarbon comprising 1, 2 or 3 carbon atoms. Aliphatic groups include alkyls, alkenyls, and alkynyls. In certain embodiments, aliphatics are optionally substituted. Aliphatic groups include, but are not limited to, methyl, ethyl, propyl, isopropyl.

The polar group can be, but is not limited to —OH, —NH$_2$, —C═O, —COOH and the like. The ligand comprising a binding moiety for binding to the metal particle can also include aromatic groups, such as a phenyl or an optionally substituted phenyl group. Examples, of suitable ligands which comprise a binding moiety for binding to the metal particle include, but are not limited to dimethylamine, diethylamine, ethanethiol, mercaptoacetic acid or 4-mercaptobenzoic acid.

The ratio of Raman active molecule to ligand comprising a binding moiety for binding to the metal particle can be between about 1:0 to 1:1 or from 1:1 to about 0:1.

In another aspect, the present invention refers to a method of manufacturing a Raman active composite material in which the metal particles are anisotropically encapsulated, wherein the step of providing the solution comprising a metal particle, an organic solvent, an amphiphilic polymer, a ligand comprising a binding moiety for binding to the metal particle and a Raman active molecule comprises:
mixing a metal particle with a solution comprising an organic solvent, an amphiphilic polymer, and a ligand comprising a binding moiety for binding to the metal particle; and
adding a Raman active molecule to the solution.

The Raman active molecule used in this method can be dissolved in an organic solvent that is miscible with water. Dissolving the Raman active molecule in an organic solvent can help to avoid that the ligands comprising a binding moiety for binding to the metal particle need to be used in the solid form, which could induce particle aggregation. If this solvent is different from the main solvent for the encapsulation, minimal volume of this solvent is used to avoid complication due to changes in solvent properties. Alcohols, such as ethanol, propanol, or butanol; acetone, or acetonitrile, to name only a few, can be used.

The Raman active molecule is added to the solution after mixing the metal particle with a solution comprising an organic solvent, an amphiphilic polymer, and a ligand comprising a binding moiety, such as a non-hydrophobic ligand, for binding to the metal particle. This ensures that the competition between the Raman active molecule and the ligand comprising a binding moiety for binding to the metal particle starts simultaneously.

In one embodiment, a method is described in which the anisotropic encapsulation of aggregates of metal particle is desired. In this method, the metal particle is not dissolved in an alcohol but in an acidic solution. In this embodiment, the step of providing the solution comprising a metal particle, an organic solvent, an amphiphilic polymer, a ligand comprising a binding moiety for binding to the metal particle and a Raman active molecule comprises:
mixing a metal particle dissolved in an acidic solution with a solution comprising an organic solvent, a Raman active molecule, and a ligand comprising a binding moiety for binding to the metal particle;
incubating the solution; and
adding an amphiphilic polymer to the solution.

Acidifying of the solution comprising the metal particle can be carried out using acids already described herein, such as HCl, $HNO_3$, $H_2SO_4$, $HClO_4$, HBr, HCOOH or $CH_3COOH$. The final pH in the acidified solution can be between about 0 to 5 or between about 2 to 4.

The incubation step referred to in this method allows aggregation of the metal particles. The incubation step can be carried out at a temperature between about 0° C. to about 100° C. Lower temperatures will generally delay the process time but will also lead to the coating of the metal particle with a Raman active molecule. The incubation step can also be carried out at a temperature of between about 30° C. to about 100° C. to increase the, or between about 40° C. to about 100° C., or between about 40° C. to about 80° C., or between about 40° C. to about 60° C. or at a temperature about 30, 40, 50, 60, 70, 80, 90 or 100° C. The time for the incubation can be between about 30 min to about 4 h, or between about 1 h to about 4 h, or between about 2 h to about 4 h, or between about 2 h to 3 h or for a time about 30 min, 1 h, 2 h, 3 h or 4 h.

The methods described herein can further include the step of binding the amphiphilic polymer of the Raman active composite material to a recognition moiety. In one embodiment, this step can be carried out after formation of the amphiphilic polymer shell or before mixing the amphiphilic polymer into the solutions referred to herein.

A Raman active composite material as described herein can for example be used within a microorganism, in particular a cell. The presence of the amphiphilic polymer allows internalization into a respective microorganism, including a cell. Depending on any moiety or molecule that may be linked to the amphiphilic polymer the Raman active composite material may also be directed to a selected intracellular compartment, structure, organelle or other location. The amphiphilic polymer used may also include groups or moieties that are capable of directing the respective Raman active composite material to a selected intracellular location. In typical embodiments where any such molecule or moiety with a location-directing function such as an immunoglobulin, or a fragment thereof, or a ligand of a receptor, is absent and the water-soluble Raman active composite material is allowed to enter a cell the Raman active composite material is at least largely locating inside the cytoplasm. Where the polymer for example includes multivalent amine groups, a corresponding water-soluble nanocrystal is capable of disrupting endosomal organelles (Duan, H., & Nie, S., *J. Am. Chem. Soc.* (2007) 129, 11, 3333-3338). Cytotoxic effects sometimes observed with metal particles can be avoided with a respective selection of the water-soluble amphiphilic polymer. This is due to the fact that cytotoxicity is dependent on the molecules present on the surface of a metal particle rather than the metal particle itself (Hoshino, A., et al., *Nano Letters* (2004) 11, 2163-2169). Accordingly a Raman active composite material can be used in a variety of biological and medical applications, including as an intracellular probe, for instance for immunofluorescence or ultrastructural imaging (see e.g. King, J., et al., *Microsc. Microanal.* (2008) 14, Suppl 2, 702-703).

In another embodiment the present invention may refer to a Raman active composite material, as disclosed herein, that is conjugated to a molecule having binding affinity for a given analyte. By conjugating the Raman active composite material to a molecule having binding affinity for a given analyte, a marker compound or probe is formed. In such a probe, the Raman active composite material serves as a label or tag which emits radiation, for example in the visible or near infrared range of the electromagnetic spectrum that can be used for the detection of a given analyte.

In principle any analyte can be detected for which a specific binding partner exists that is able to at least certain degree specifically bind to the analyte. Examples of suitable analytes can include in one embodiment, prokaryotic or eukaryotic cells, malign eukaryotic cells, organelles, nucleic acids, proteins, viruses, to name only a few. The analyte can be a chemical compound such as a drug (e.g. Aspirin®) or Ribavirin), or a biochemical molecule such as a protein (for example, an antibody specific for troponin or a cell surface protein) or a nucleic acid molecule. When coupled to an appropriate molecule with binding affinity (which is also referred to as the analyte binding partner) for an analyte of interest, such as Ribavirin, the resulting probe can be used for example in a fluorescent immunoassay for monitoring the level of the drug in the plasma of a patient. Another example is a conjugate of the Raman active composite material with streptavidin.

The analyte can also be a complex biological structure including, but not limited to, a virus particle, a chromosome or a whole cell. For example, if the analyte binding partner is a lipid that attaches to a cell membrane, a conjugate comprising a Raman active composite material linked to such a lipid can be used for detection and visualization of a whole cell. For purposes such as cell staining or cell imaging, a nanoprobe emitting or scattering visible light is preferably used. In accordance with this disclosure the analyte that is to be detected by use of a marker compound that comprises a Raman active composite material conjugated to an analyte binding partner is preferably a biomolecule.

Therefore, in a further embodiment, the molecule has binding affinity for the analyte which can include, but is not limited to a protein, a peptide, a compound having features of an immunogenic hapten, a nucleic acid, a carbohydrate or an organic molecule. The protein employed as analyte binding partner can be, for example, an antibody, an antibody fragment, a ligand, avidin, streptavidin or an enzyme. Examples of organic molecules are compounds such as biotin, digoxigenin, serotronine, folate derivatives, antigens, peptides, proteins, nucleic acids and enzymes and the like. A nucleic acid may be selected from, but not limited to, a DNA, RNA or PNA molecule, a short oligonucleotide with 10 to 50 bp as well as longer nucleic acids.

In a further embodiment, multiple SERS probes are used to separately label multiple analytes, such as for multiplexed detection. This allows the simultaneous detection and tracking of multiple different targets of interest. For example, 10 different antibodies that each has specific affinity for their distinctive cancer cells could be attached to 10 different SERS probes, by performing 10 separate reactions. The subsequent SERS mapping would reveal the localization of these 10 types of cancer cells.

The Raman active composite material can also be used in combination with other already known labels or probes, such as quantum dots. When using the Raman active composite material described herein together with quantum dots, it is for example possible to encapsulate the quantum dots with amphiphilic polymers using the methods described herein. It is also possible to form aggregates of quantum dots and Raman ligand coated metal particles and encapsulating them together as illustrated for example in FIGS. 8 and 9D.

By "consisting of" is meant including, and limited to, whatever follows the phrase "consisting of". Thus, the phrase "consisting of" indicates that the listed elements are required or mandatory, and that no other elements may be present.

By "comprising" it is meant including, but not limited to, whatever follows the word "comprising". Thus, use of the term "comprising" indicates that the listed elements are required or mandatory, but that other elements are optional and may or may not be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

General Description of the Manufacturing Method for Raman Active Composite Materials In a first example, AuNPs (NP=nanoparticle) or AgNPs were incubated with a hydrophobic Raman reporter (such as a Raman reporter shown in FIG. 2 or 6) in dimethylformamide (DMF) at 60° C. to render the NP surface hydrophobic. After the solution was cooled down, an amphiphilic polymer, such as $PS_{154}$-block-$PAA_{60}$ was added. Afterwards water (final volume ratio DMF/$H_2O$=4.5) was added. The amount of amphiphilic polymer added is secondary as long as enough of the polymer is added to ensure encapsulation of the metal nanoparticle coated with the Raman reporter molecule. The mixture was heated to 110° C. for 2 hrs and then slowly cooled down in the oil bath. As the critical micelle concentration slowly decreased with temperature, the amphiphilic polymer was excluded from solution and self-assembled into spherical micelles that sometimes include the hydrophobically functionalized NPs. FIG. 3a shows the TEM image of a sample prepared by this method; the polymer appeared white against the $(NH_4)_6Mo_7O_{24}$ negative stain. Both empty micelles and micelle-encapsulated AuNPs were observed. Remarkably, nearly all AuNPs observed (>99%) were singly encapsulated by polymer micelles.

The uniform diameter of the empty micelles as well as the uniform thickness of the micellar shells are consistent with a thermodynamically controlled self-assembly process. In this method, the reactant mixture was heated for 2 h followed by slow cooling (~2 h) to ensure near-equilibrium conditions.

The nanoprobes can be easily isolated by direct centrifugation. After synthesis, the reaction mixture was first diluted in water (14 times by volume) to trap the polymer micelles in a kinetically stable state. Repeated centrifugation at 16000 g and resuspension in water gave NPs free of DMF and empty micelles (FIG. 3b). The NPs did not aggregate during the repeated purification, even though the polymer shells were not chemically cross-linked. Without being bound by theory, it is assumed that this extraordinary stability could be due to the long hydrophilic PAA blocks of the polymer that brought in extra negative charges on the NPs. The simple purification process allows for efficient isolation of large quantities of a Raman active nanocomposite material. Using this method, gold and silver NPs of various sizes and morphologies were successfully functionalized by SERS reporters, encapsulated, and purified (FIG. 3b-f).

In previous reports that prepared silica-coated, analyte-tagged NPs, two competing ligands have to be used to bind metal NP surface: a SERS-active reporter and a vitreophilic coupling agent such as APTMS ((Mulvaney, S. P., Musick, M. D., et al., 2003, supra). In contrast, only one ligand (any one of FIGS. 2-1 to 2-4) was used in this preparation to fully cover the surface of AuNPs. In addition to accommodating more reporter molecules per NP, this design avoids the problem of the mutually exclusive ligand binding competition that likely results in uneven loading of reporter molecules on individual NPs. In this system, the ensemble-averaged SERS signature is a close representation for the individual nanoparticles, considering that (a) a single ligand covers uniformly on the surface of the metal NPs; (b) all NPs have a well-defined core/shell structure with uniform shell (amphiphilic polymer) thickness; and (c) each polymer micelle contains only one metal NP.

Ensemble-averaged SERS signals from the Raman active composite materials were characterized by solution Raman spectroscopy. FIG. 4A shows the SERS signals of 2-naphthalenethiol on AuNPs ($d_{av}$=14, 21, 38, 51 and 62 nm). No extra peak was observed that could be assigned to the SERS of polystyrene (PS) of the amphiphilic polymer (e.g. PS-block-PSPAA), suggesting that most of the NP surface was covered by the Raman reporter. It is difficult to directly compare the SERS intensities observed in our experiments with those reported in the literature, because in most reports the degree of NP aggregation and the concentration of SERS reporters were not available. In our system, the full coverage of 2-naphthalenethiol on NPs is expected to give only slightly stronger SERS signals, while the absence of SERS "hot-spots" likely gave rise to weaker signals. The high percentage of single encapsulation (>99%) of AuNP coverd with 2-naphthalenethiol and amphiphilic polymer gave the rare opportunity to estimate the ensemble-averaged enhancement factors unambiguously.

Figure 5:
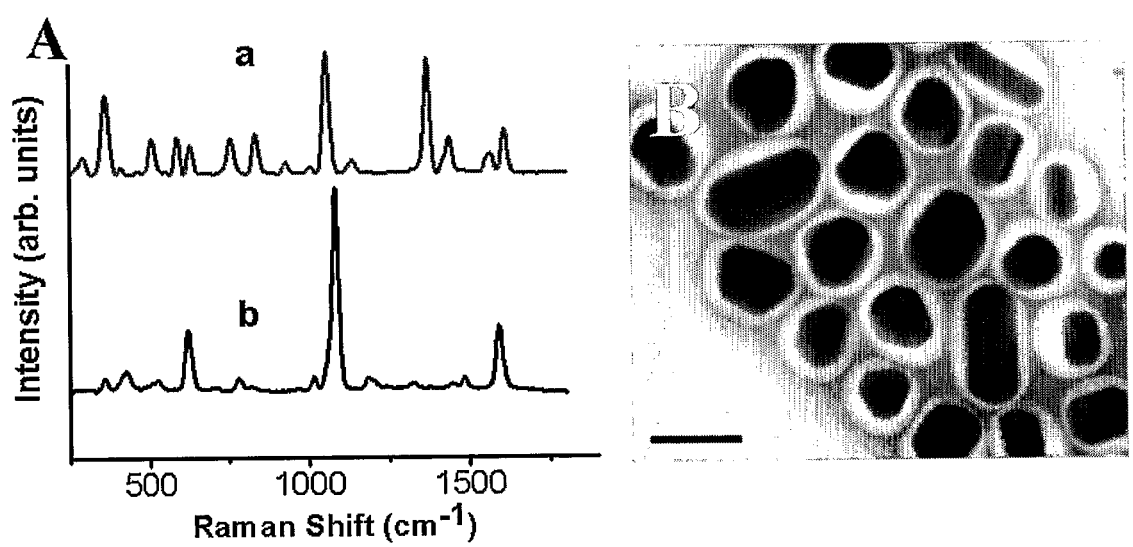
FIG. 5A shows SERS spectra of two different Raman active composite materials using (a) 2-naphthalenethiol and (b) 4-ethylbenzenethiol as Raman active molecules.
FIG. 5B show a TEM image of AgNPs coated with 4-ethylbenzenethiol and encapsulated with an amphiphilic polymer. The scale bar is 100 nm.

In order to better evaluate the SERS intensities observed in this system, the signals were normalized against the total surface area of the NPs, which can be estimated based on the total particle concentrations and average sizes. Assuming that all AuNP surface were (111) facet and that one ligand were coordinated to every three Au atoms on the (111) surface, the total moles of 2-naphthalenethiol in each sample could be roughly estimated. Comparing with solution Raman of free 2-naphthalenethiol in acetone, the enhancement factors were estimated to be $7.2 \times 10^4$, $1.2 \times 10^5$, $1.0 \times 10^6$, $6.2 \times 10^6$ and $2.2 \times 10^7$, for AuNPs for 14, 21, 38, 51 and 62 nm diameters, respectively (Table 1). It is clear that the enhancement factor increases significantly with increasing AuNP diameter (FIG. 4B). Significantly larger enhancement was observed on AgNPs. The ensemble-averaged enhancement factor for AgNP covered with 2-naphthalenethiol and an amphiphilic polymer ($d_{av}$=43.4 nm) was estimated to be around 1 to about $2 \times 10^8$ (ignoring the difference in contributions from the silver nanorods in the sample), nearly 100 times stronger than that of AuNPs of similar size.

materials have similar core/shell structures as 2-naphthalenethiol-covered AuNPs encapsulated with an amphiphilic polymer (FIG. 5B) but present different spectroscopic signatures (FIG. 5A-b). The signal intensity of 4-ethylbenzenethiol coated AgNP encapsulated with an amphiphilic polymer is comparable with that of 2-naphthalenethiol-covered AgNPs encapsulated with an amphiphilic polymer but the signal of triphenylphosphine-covered AgNPs encapsulated with an amphiphilic polymer was slightly weaker, giving peaks at 469, 528, 791, 1009, 1384 and 1578 $cm^{-1}$.

Experimental

Materials: All chemical reagents were used without further purification. Hydrogen tetrachloroaurate(III) hydrate ($HAuCl_4 \cdot H_2O$), 99.9% (metals basis Au 49%) was purchased from Alfa Aesar; amphiphilic diblock copolymer

TABLE 1

Estimates for SERS enhancement factors.

| | Average diameter (nm)[a] | Calculated volume per NP ($nm^3$)[b] | Calculated surface area per NP ($nm^2$)[b] | Weight of each NP (g/mole) | Number of ligands per each NP[c] | As-synthesized NP concentration (pM)[d] | Raman active composite material concentration (pM)[e] | Equivalent concentration of 2-naphthalenethiol (nM) | Enhancement Factor[f] |
|---|---|---|---|---|---|---|---|---|---|
| AuNPs | 13.7 | 1358.2 | 593.1 | $1.58 \times 10^{10}$ | 2752 | 38.75 | 27.58 | 75.90 | $7.2 \times 10^4$ |
| | 21.0 | 4856.0 | 1386.8 | $5.64 \times 10^{10}$ | 6435 | 10.86 | 6.45 | 41.51 | $1.2 \times 10^5$ |
| | 37.9 | 28572.4 | 4519.8 | $3.37 \times 10^{11}$ | 20974 | 1.82 | 1.28 | 26.85 | $1.0 \times 10^6$ |
| | 51.0 | 69578.5 | 8180.9 | $8.19 \times 10^{11}$ | 37962 | 0.75 | 0.73 | 27.71 | $6.2 \times 10^6$ |
| | 62.1 | 125574.9 | 12127.0 | $1.46 \times 10^{12}$ | 56274 | 0.42 | 0.35 | 19.70 | $2.2 \times 10^7$ |

[a]Measured from TEM images using ImageJ.
[b]It is assumed that all NPs in a given sample have uniform diameter with a regular spherical shape.
[c]Assuming that all AuNP surface were (111) facet and that one ligand were coordinated to every three Au atoms on the (111) surface.
[d]NP concentrations in the as-synthesized solution were calculated based on the moles of starting materials used and average weight of each NP.
[e]Raman active composite material concentrations of purified samples of AuNP covered with 2-naphthalenethiol were calculated based the AuNP plasmon absorption bands.
[f]Enhancement factors were based on the Raman intensity of free 2-naphthalenethiol in acetone and SERS intensity of 2-naphthalenethiol on the AuNP surface.

The stability of the Raman active composite materials was tested by exposing them to adverse conditions. Salt medium was known to cause aggregation of citrate-stabilized AuNPs, as the increased ionic strength weakens the charge-repulsion between the NPs. In contrast, the nanoprobes prepared by our method can tolerate up to 0.1 M NaCl without aggregation. No change of SERS intensity was observed with and without the salt media. This allows the use of the nanoprobes in buffer solutions often encountered in biomedical applications. The polymer shell can also provide protection against chemical oxidation. Because 2-naphthalenethiol-coated AuNPs are insoluble in water, AuNPs coated with 4-mercaptobenzoic acid was used as a comparison. $KHSO_5$ (oxone) is one of the strongest commercially available oxidants ($E°$=1.4 V vs NHE). When it was added to AuNPs incubated with excess 4-mercaptobenzoic acid ([oxone]=20 mM), the red colour of the solution quickly faded, and precipitates formed at the bottom of the vial. Presumably, the thiol groups of 4-mercaptobenzoic acid were forced to dissociate from AuNPs as they were oxidized. However, under the same treatment, 2-naphthalenethiol-coated AuNP encapsulated with an amphiphilic polymer were stable for weeks without significant loss of the red colour or of the SERS signal intensity. These results demonstrated that the polymer shell is nearly impermeable to the ionic oxidant, protecting the Raman active composite material during various applications.

Figure 2:
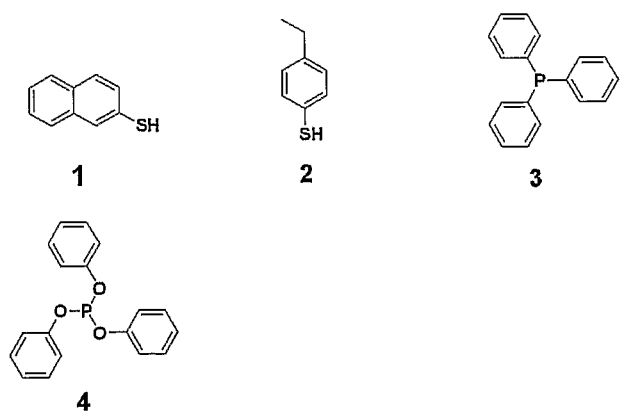
FIG. 2 shows four different examples of Raman active molecules which have been used for the Raman active composite material referred to herein, namely 2-naphthalenethiol (FIG. 2-1), 4-ethylbenzenethiol (FIG. 2-2), triphenylphosphine (FIG. 2-3) and friphenylphosphite (FIG. 2-4).
Figure 3:
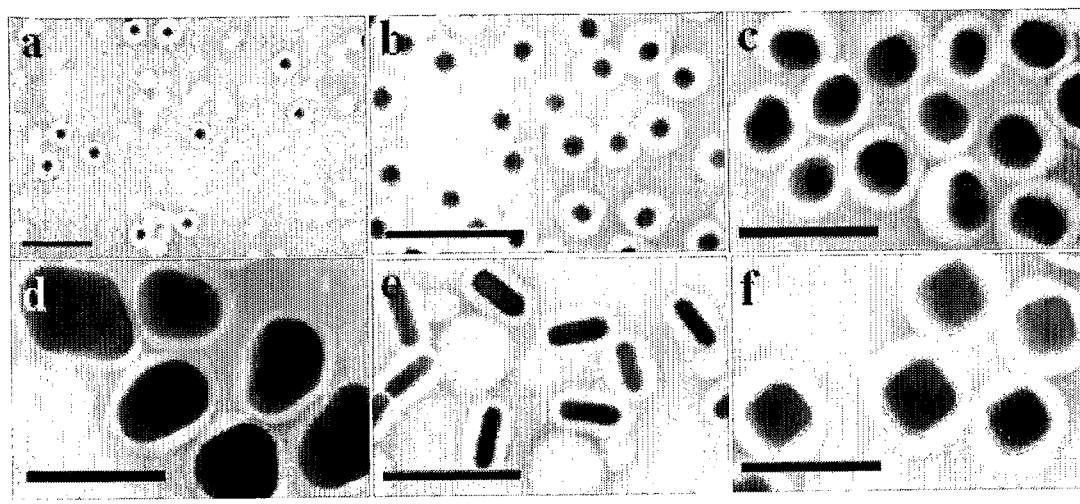
FIG. 3 shows TEM images of Raman active composite materials. The metal nanoparticle of the Raman active composite material is encapsulated by $PS_{154}$-block-$PAA_{60}$, showing AuNPs of 14 nm before (a) and after purification (b), AuNPs of 38 nm (c) and 62 nm (d), gold nanorods (e) and silver nanocubes (f). All scale bars are 100 nm.
Figure 4:
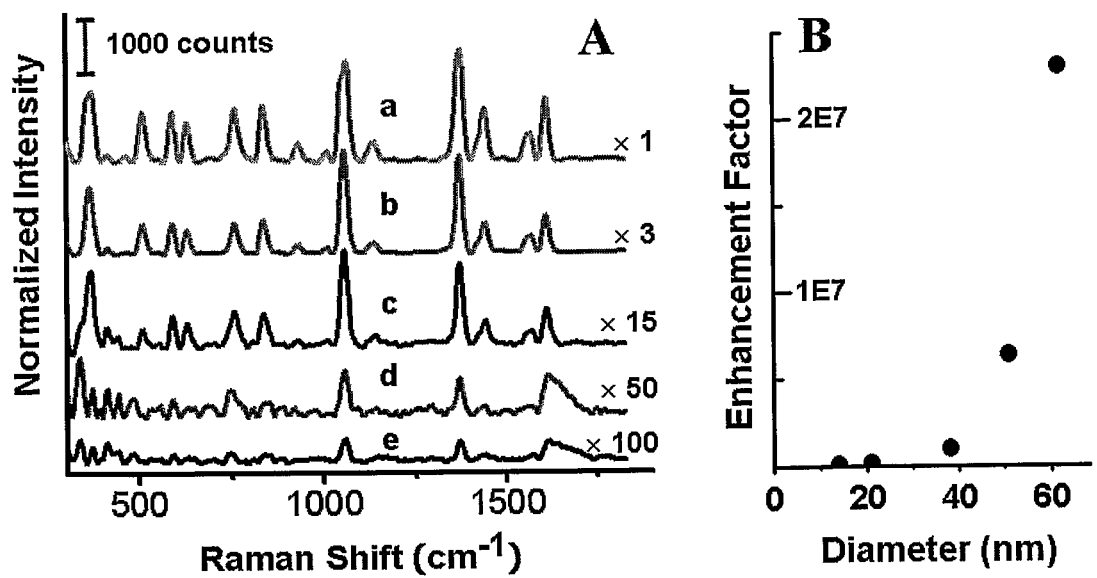
FIG. 4 shows (A) Raman spectra of an AuNP covered with 2-naphthalenethiol and an amphiphilic polymer of various AuNP sizes: (a) 62 nm, (b) 51 nm, (c) 38 nm, (d) 21 nm and (e) 14 nm; (B) Dependence of the ensemble-averaged enhancement factor on the size of AuNPs, showing the estimated factors based on (A).

The polymer encapsulation process was demonstrated in further experiments for the Raman active molecules shown in FIGS. 2-2 and 2-3. The resulting Raman active composite polystyrene-block-poly(acrylic acid) ($PS_{154}PAA_{60}$, $M_n$=16000 for the polystyrene block and $M_n$=4300 for the poly(acrylic acid) block, $M_w/M_n$=1.15 and $PS_{144}$-block-$PAA_{28}$, $M_n$=15000 for the PS block and $M_n$=1600 for the PAA block, $M_w/M_n$=1.11) was obtained from Polymer Source, Inc.; DMF, 99.8% was purchased from Tedia Company, Inc. Deionizied water (resistance>18 MΩ $cm^{-1}$) was used in all of our reactions. All other chemicals were purchased from Aldrich. Copper specimen grids (200 mesh) with formvar/carbon support film (referred to as TEM grids in the text) were purchased from Electron Microscopy Sciences; AuNPs were prepared as described in (Frens, G., 1973, Nature Phys. Sci., vol. 241, pp. 20); AuNRs were prepared as described in (Nikoobakht, B., El-Sayed, M. A., 2003, Chem. Mat., vol. 15, pp. 1957) and Ag nanocubes (AgNC) were prepared as described in (Siekkinen, A. R., McLellan, J. M., 2006, Chem. Phys. Lett., vol. 432, pp. 491).

General Methods and Characterization: Raman spectra were collected from suspended NP samples in a cuvette (pathlength=1.00 cm) on an R-3000HR spectrometer (Raman Systems, Inc, R-3000 series) using Red LED laser ($\lambda$=785 nm). UV-vis spectra were collected on a Cary 100 UV-Vis spectrophotometer. TEM images were collected from a FEI EM 208S Transmission Electron Microscopy (Philips) operated at 100 kV.

Preparation of TEM Samples: $(NH_4)_6Mo_7O_{24}$ was used as a negative stain (3.4 mM) in all TEM images, so that empty micelles and polymer shells appeared white against a dark background. TEM grids were treated by oxygen plasma in a Harrick® plasma cleaner/sterilizer for 1 min to improve the surface hydrophilicity. A sample solution was carefully mixed with stain solution on the surface of a plastic petridish, forming a small bead; a TEM grid was then floated on the top of the bead with the hydrophilic face contacting the solution. The TEM grid was then carefully picked up by a pair of tweezers, wicked with filter paper to remove excess solution and finally dried in air for 5 min.

Encapsulation of nanoparticles with ligands and $PS_{154}$-b-$PAA_{60}$: In a typical reaction, 4×1.5 mL of AuNPs solution ($d_{av}$=14 nm, 4.75 nM) was concentrated to ~20 µL by centrifugation at 16000 g for 15 min. To the deep red suspension collected at the bottom of Eppendorf tubes, 715 µL DMF was added, followed by 5 µL of a Raman active molecule, such as 2-naphthalenethiol in DMF (10 mg/mL). The mixture was incubated at 60° C. for 1 hr before 80 µL $PS_{154}$-b-$PAA_{60}$ solution (8 mg/mL in DMF) and 160 µL $H_2O$ was added in sequence. The total volume of the final mixture solution was 980 µL, where the DMF/$H_2O$ volume ratio was 4.5; [AuNPs]=29.08 nM; [$PS_{154}PAA_{60}$]=32 µM and [2-naphthalenethiol]=3.82 µM. The mixture was heated to 110° C. for 2 hrs and then allowed to slowly cool down in the oil bath until room temperature was reached. The final solution was deep red and it remained stable at room temperature for months.

Same encapsulation procedures were used to prepare 4-ethylbenzenethiol-coated AuNPs encapsulated in an amphiphilic polymer and triphenylphosphine-coated AuNPs encapsulated in an amphiphilic polymer, except that 4-ethylbenzenethiol or triphenylphosphine of similar concentrations was used instead of 2-naphthalenethiol. AgNPs prepared by citrate reduction method (Frens, G., 1973, supra) were also encapsulated using this method.

The gold nanorods (AuNRs) were prepared by following El-sayed's method (Nikoobakht, B., El-Sayed, M. A., 2003, supra), concentrated by centrifugation and then resuspended in water. The silver nanocubes (AgNCs) were prepared by following Xia's method and purified by acetone washing (Siekkinen, A. R., McLellan, J. M., 2006, supra). Same encapsulation method as described above was then used to encapsulate the AuNRs and AgNCs.

Purification of the Core/Shell Raman active composite material: The Raman active composite material was purified by centrifugation to remove DMF, empty micelles and excess ligand. In a typical procedure, 100 µL of 2-naphthalenethiol-coated AuNPs encapsulated in an amphiphilic polymer in the as-synthesized solution was mixed with 1400 µL $H_2O$ in an Eppendorf tube. The mixture was centrifuged at 16000 g for 30 min so that nearly all NPs were collected at the bottom of the tube. The supernatant was discarded, and 1.5 mL $H_2O$ was added to resuspend the NPs. This centrifugation-resuspension was usually repeated twice to obtain samples free of DMF and empty micelles.

Estimation of SERS Enhancement Factors: The average sizes of AuNPs ($d_{av}$=13.7 nm, 21.0 nm, 37.9 nm, 51.0 nm and 62.1 nm) were determined from TEM images using ImageJ. As shown in Table 1, the concentrations of the as-synthesized AuNPs were calculated based on the dimensions of the NPs and the density of gold (19.3 g·$cm^{-3}$). Here it was assumed that all NPs in a given sample have uniform diameter with a regular spherical shape, although in some cases these were not strictly true. After encapsulation and purification, the concentrations of the isolated Raman active composite material was calculated by comparing the plasmon absorption peak intensity of the sample versus that of the as-synthesized samples. For convenience, we assume that all AuNP/AgNP surface were (111) facet and that one ligand were coordinated to every three Au/Ag atoms on the (111) surface. Based on the NP concentration and total surface area, total mole of 2-naphthalenethiol can be calculated. The ratio of the observed SERS intensity to the Raman intensity of equivalent concentration of free 2-naphthalenethiol in acetone gave the respective enhancement factors.

Figure 6:
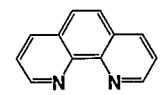
FIG. 6 shows TEM images and SERS signal of AuNPs coated with the Raman active molecules shown in FIG. 6 and encapsulated with an amphiphilic polymer in water.
Figure 6:
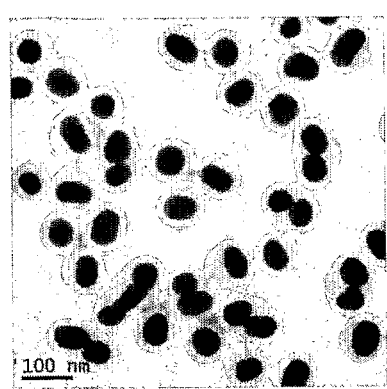
Figure 6:
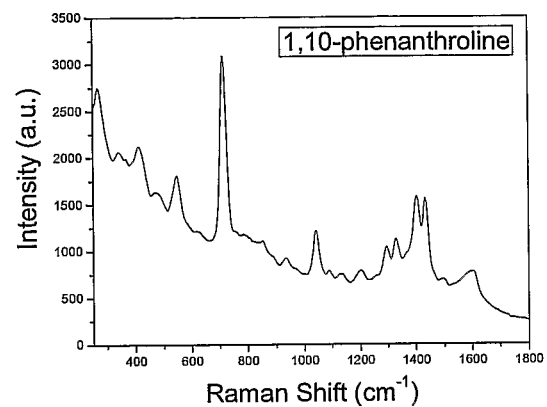
Figure 6:
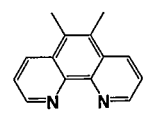
Figure 6:
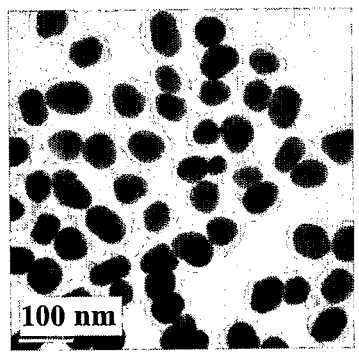
Figure 6:
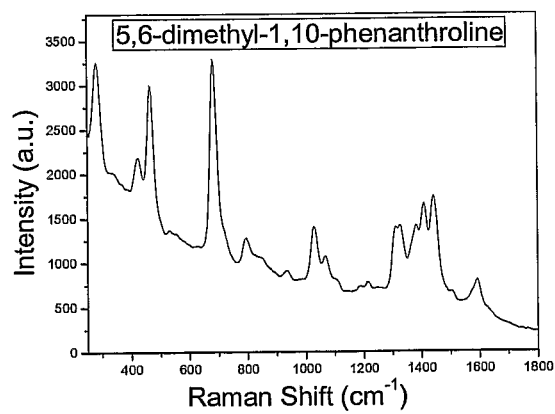
Figure 6:
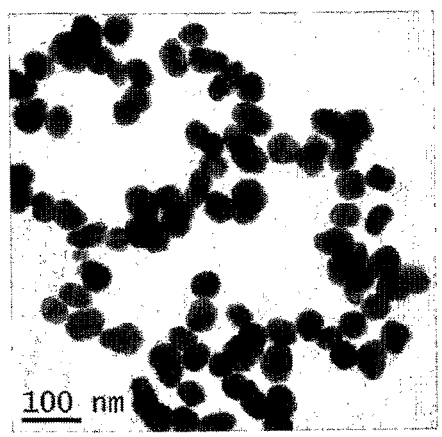
Figure 6:
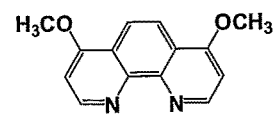
Figure 6:
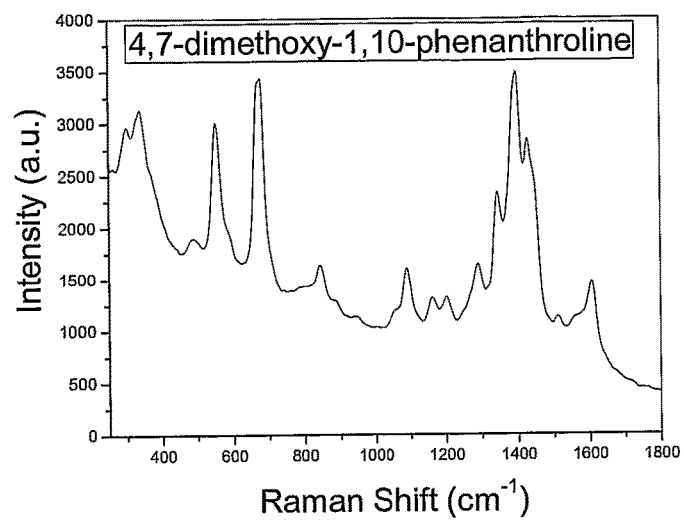
Figure 6:
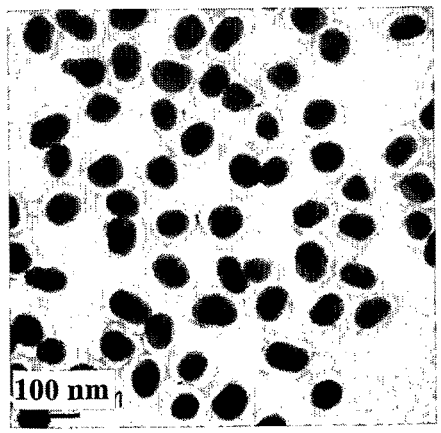
Figure 6:
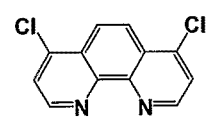
Figure 6:
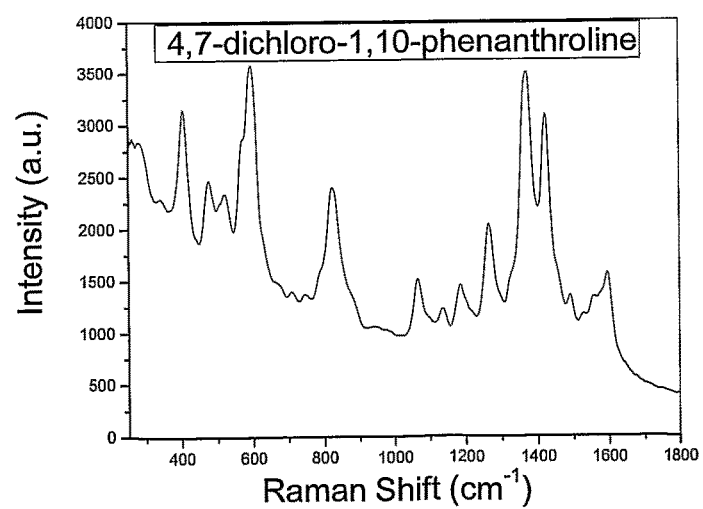
Figure 6:
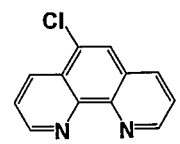
Figure 6:
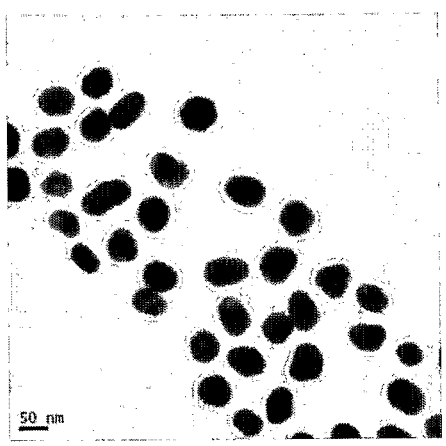
Figure 6:
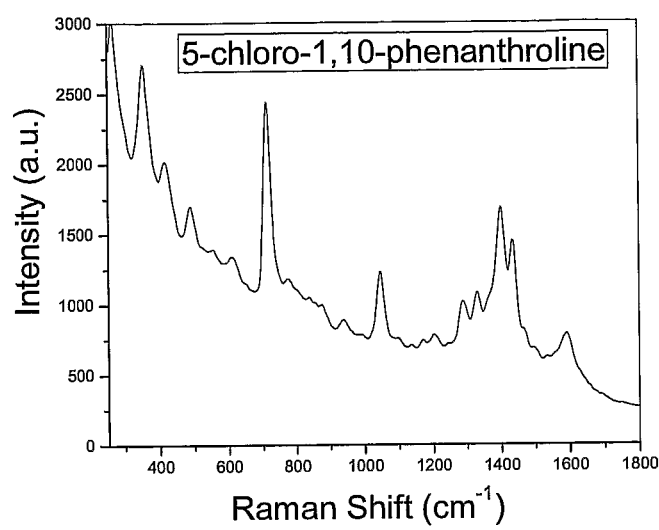
Figure 6:
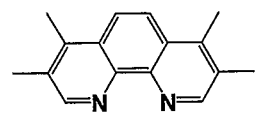
Figure 6:
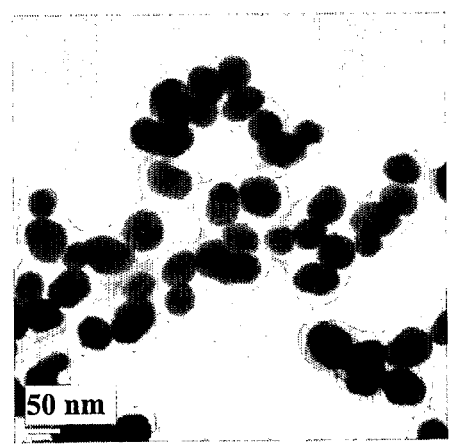
Figure 6:
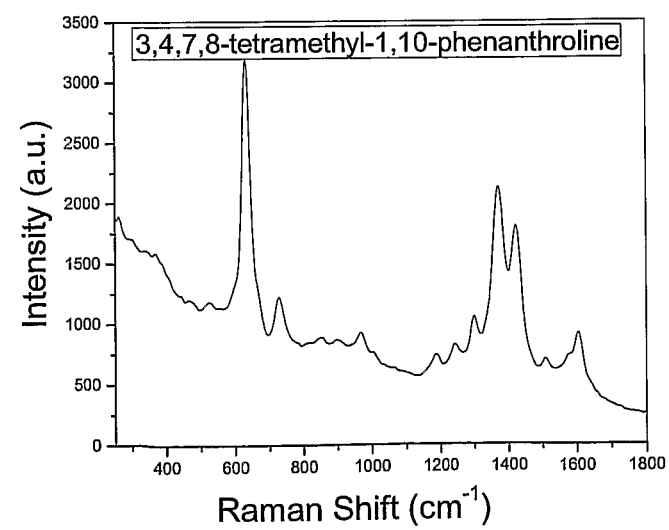
Figure 6:
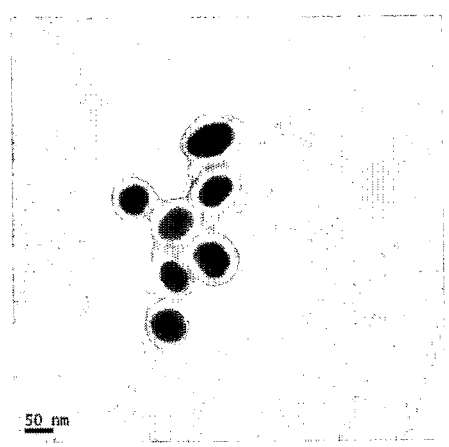
Figure 6:
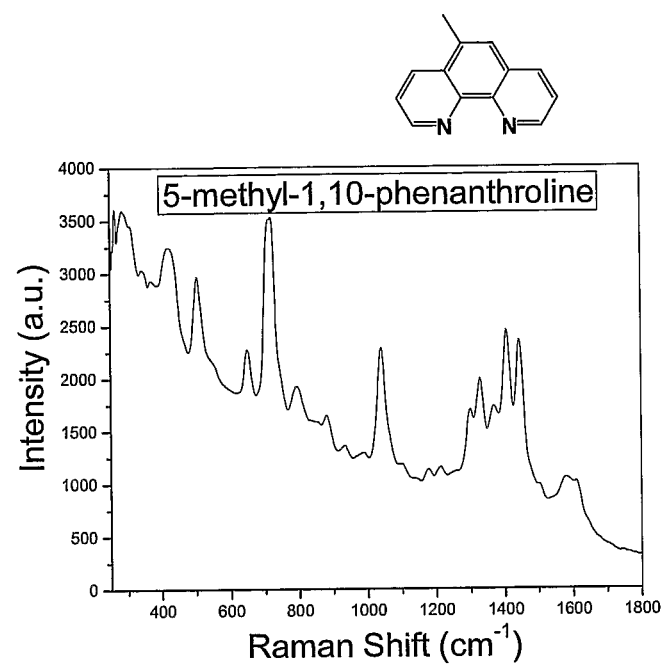
Figure 6:
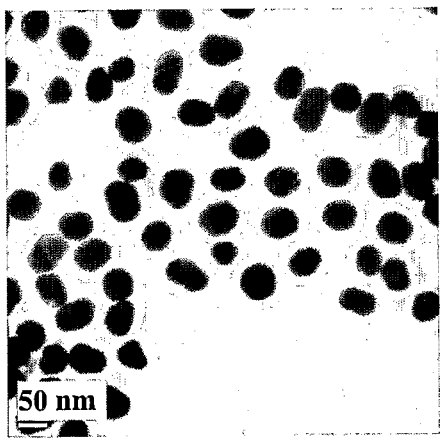
Figure 6:
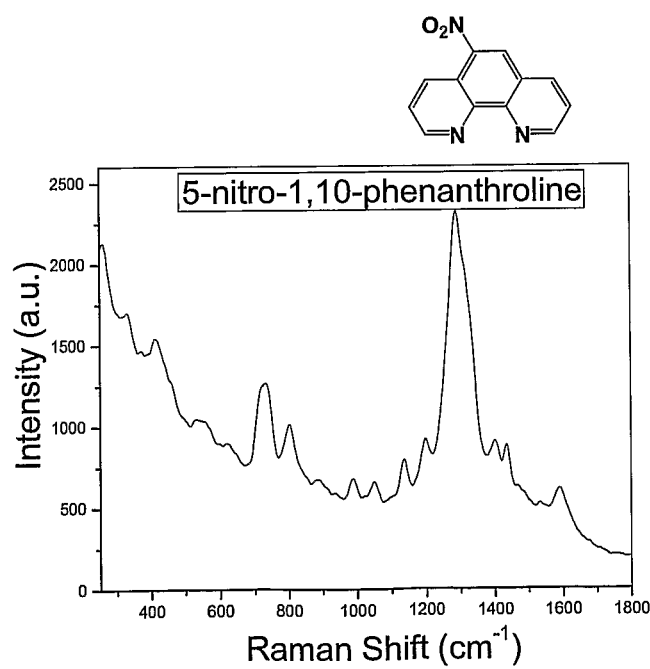
Figure 6:
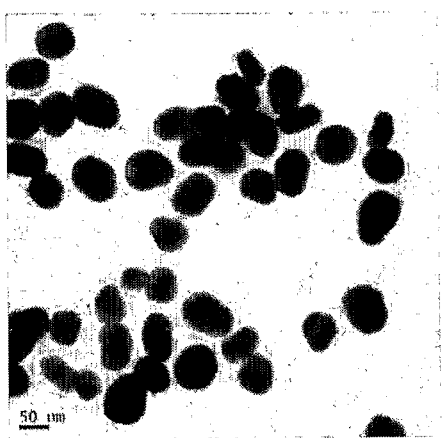
Figure 6:
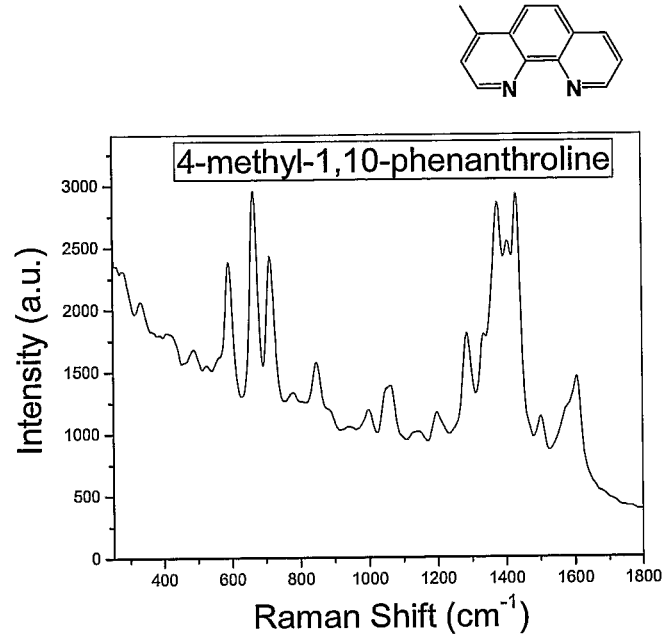
Figure 6:
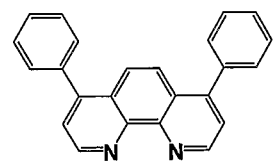
Figure 6:
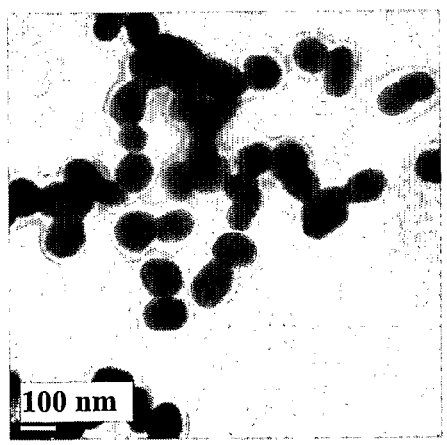
Figure 6:
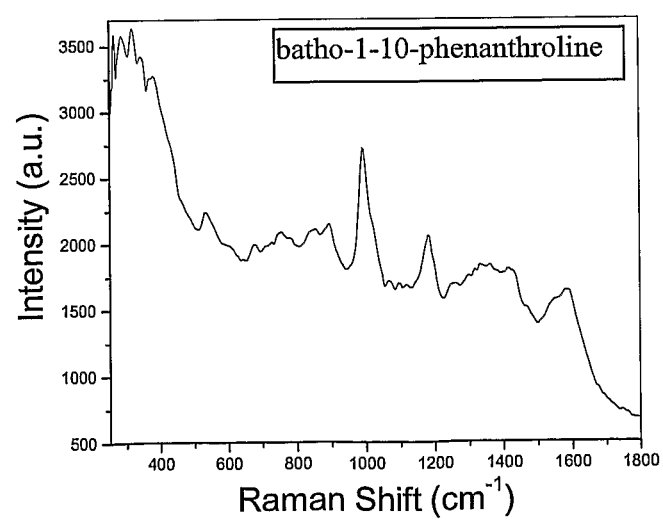
Figure 6:
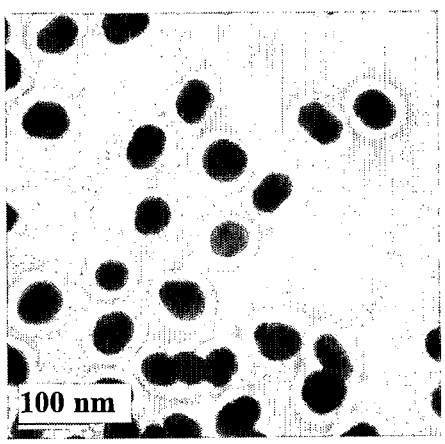
Figure 6:
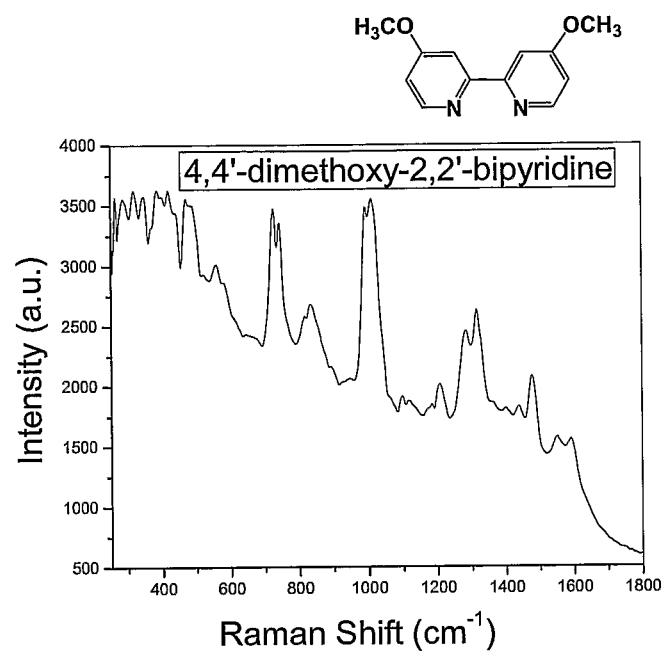
Figure 6:
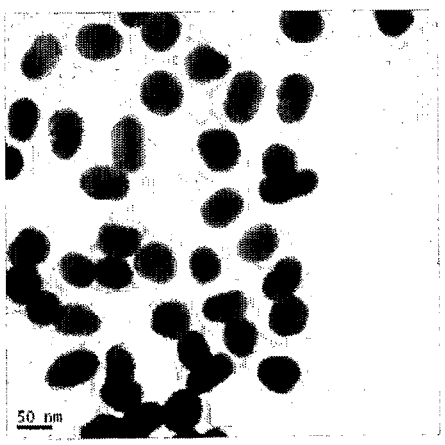
Figure 6:
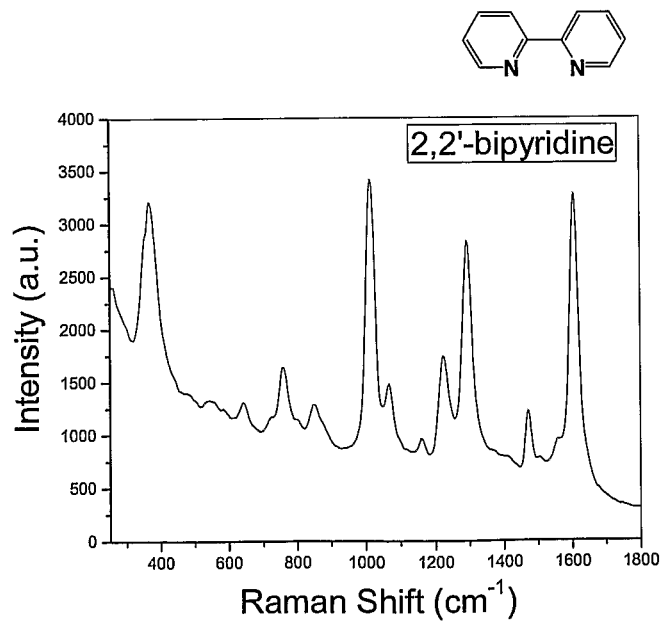
Figure 6:
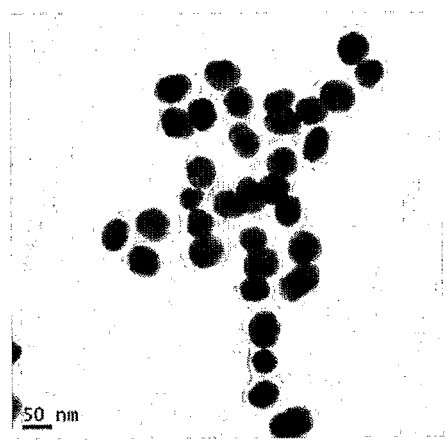
Figure 6:
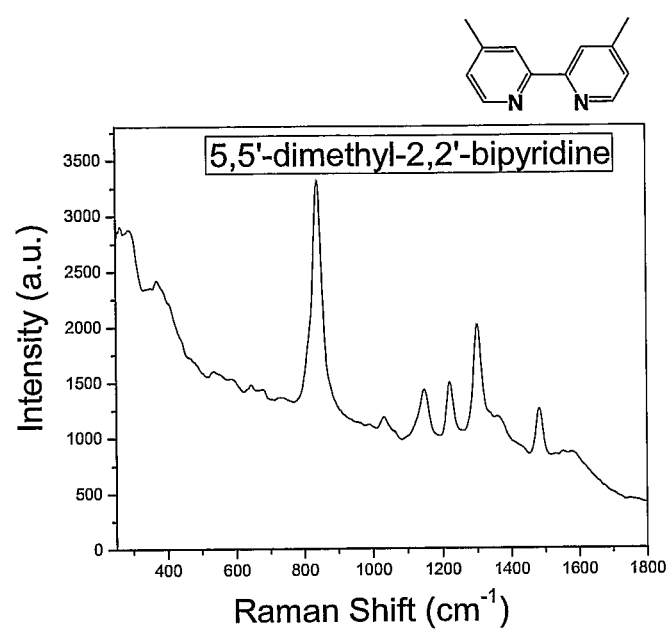
Figure 6:
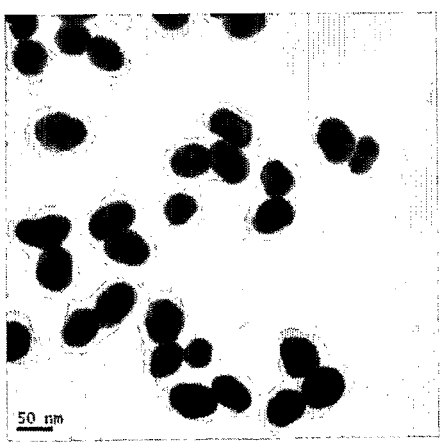
Figure 6:
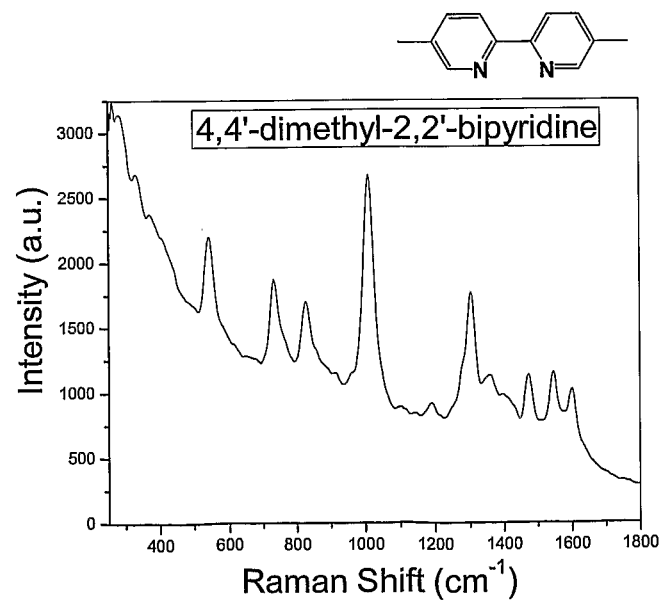
Figure 6:
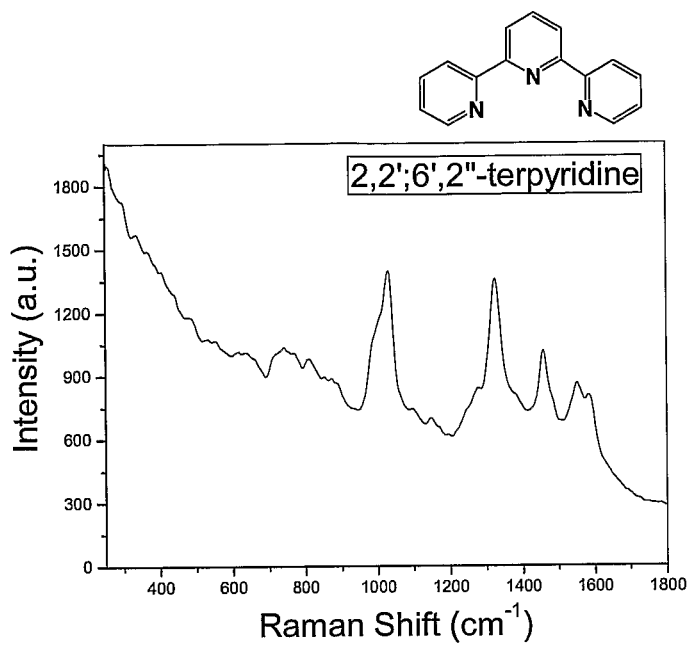
Figure 6:
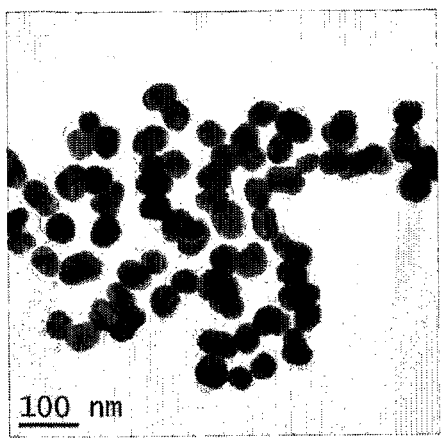
Figure 6:
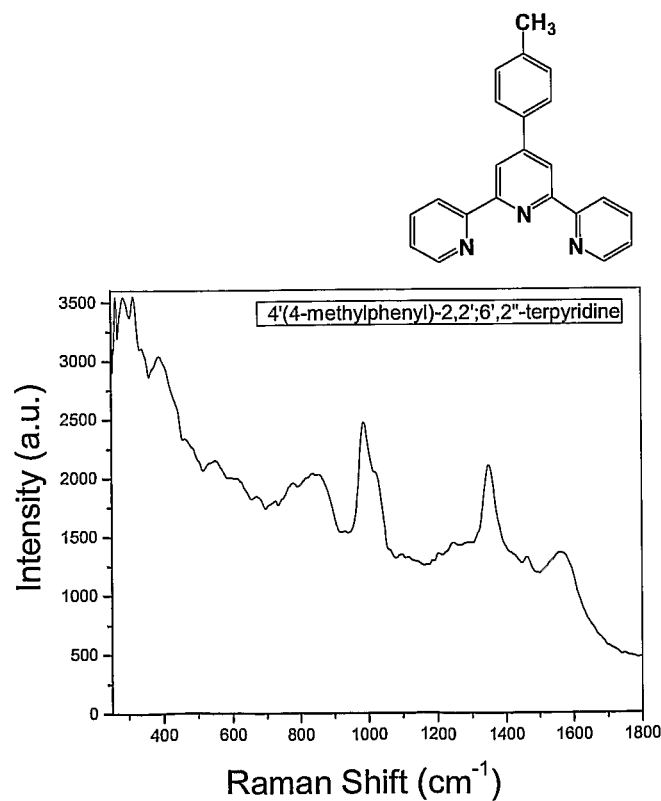
Figure 6:
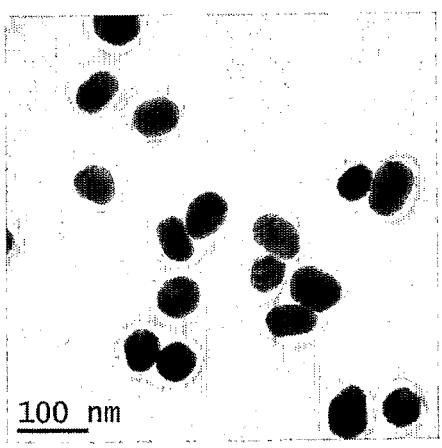
Figure 6:
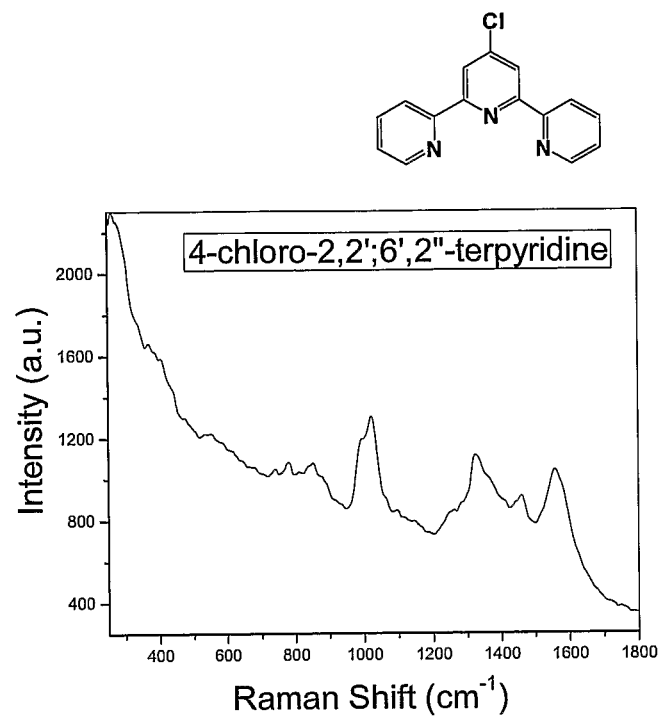
Figure 6:
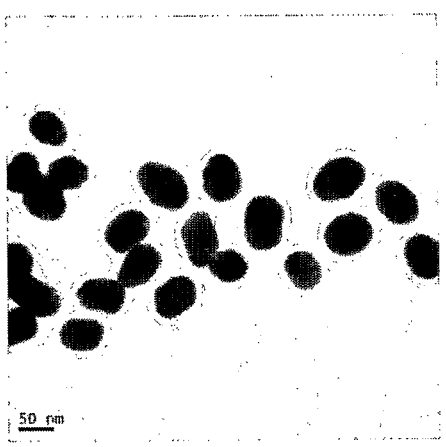
Figure 6:
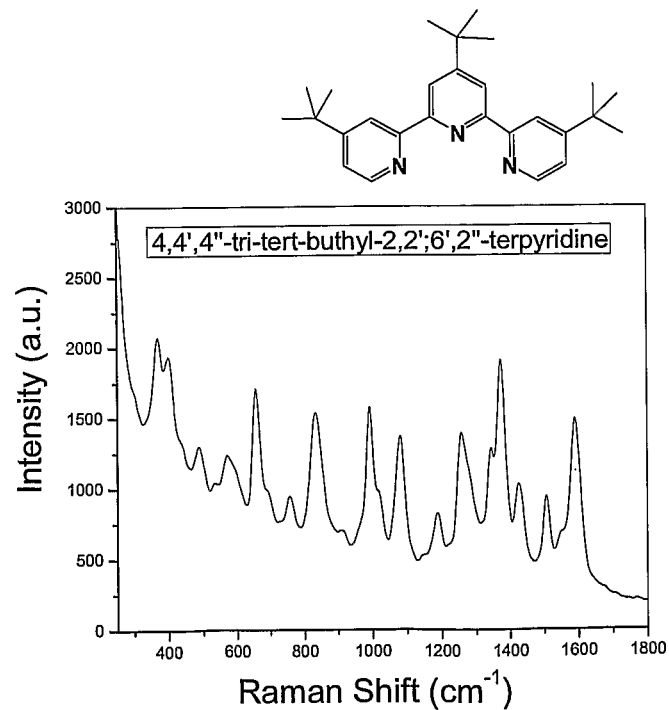
Figure 6:
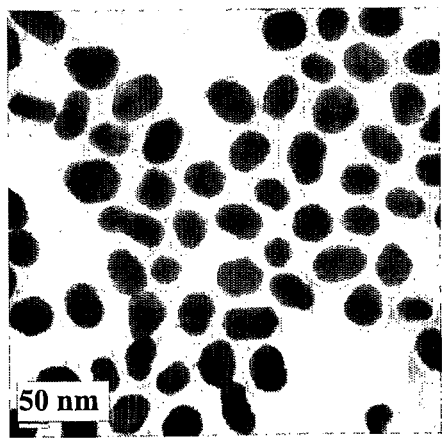
Figure 6:
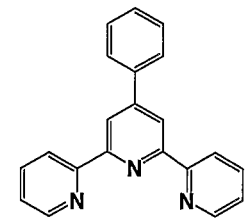
Figure 6:
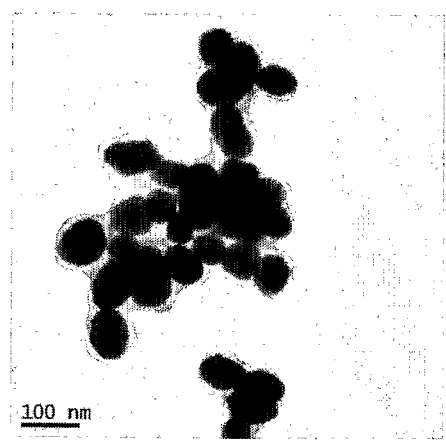
Figure 6:
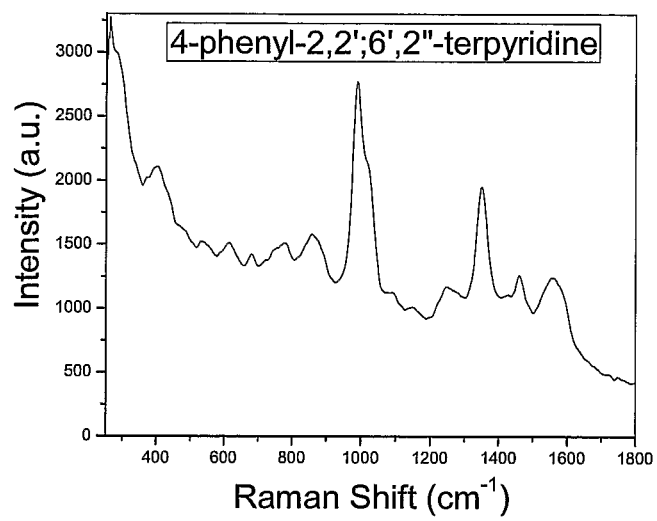
Figure 6:
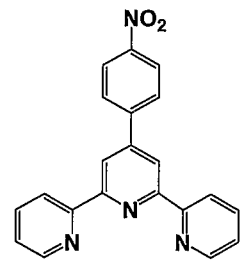
Figure 6:
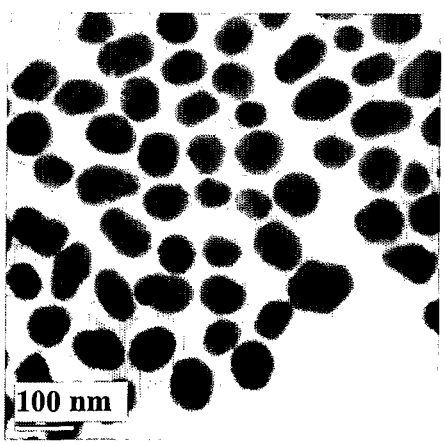
Figure 6:
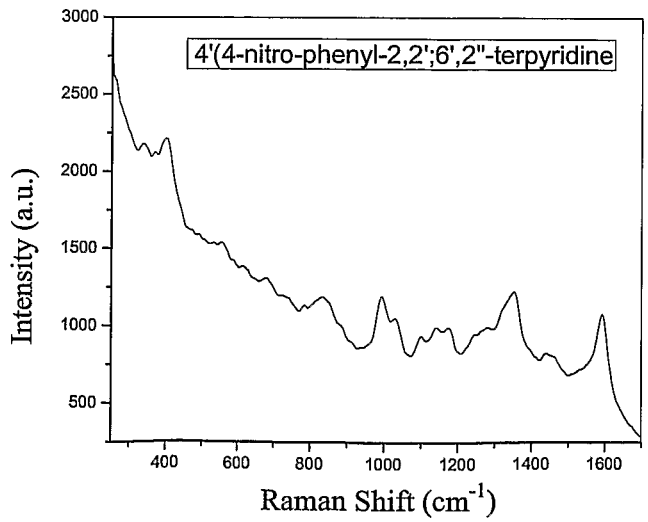
Figure 6:
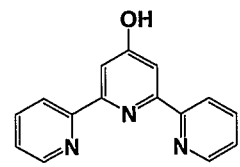
Figure 6:
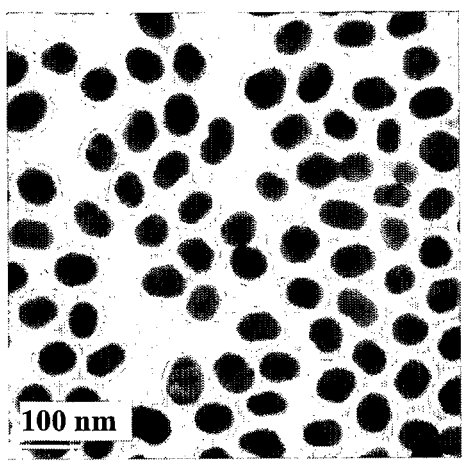
Figure 6:
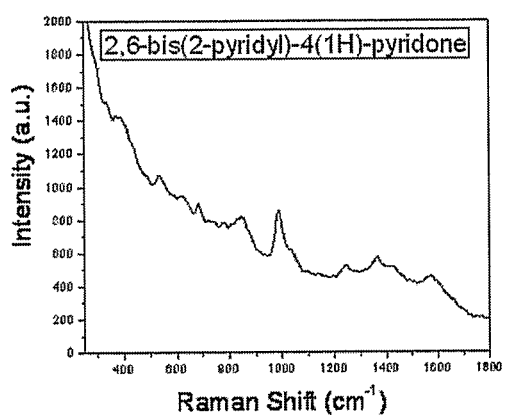
Figure 7A:
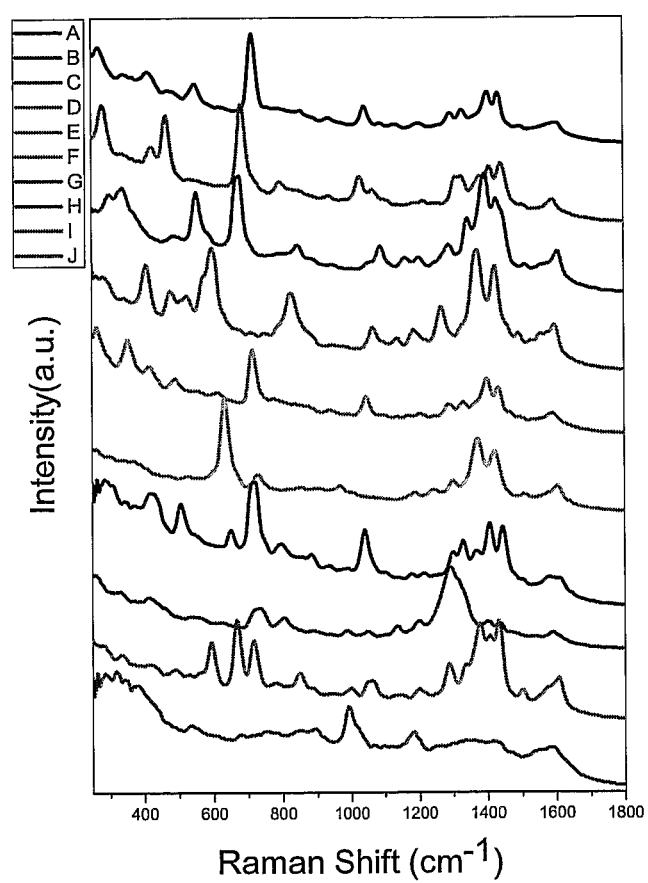
FIG. 7a shows the SERS signal of an AuNPs encapsulated with an amphiphilic polymer and coated with (A) 1,10-phenanthroline, (B) 5,6-dimethyl-1,10-phenanthroline, (C) 4,7-dimethoxy-1,10-phenanthroline, (D) 4,7-dichloro-1,10-phenanthroline, (E) 5-chloro-1,10-phenanthroline, (F) 3,4,7,8-tetramethyl-1,10-phenanthroline, (G) 5-methyl-1,10-phenanthroline, (H) 5-nitro-1,10-phenanthroline, (I) 4-methyl-1,10-phenanthroline, (J) batho-1,10-phenanthroline.
Figure 7B:
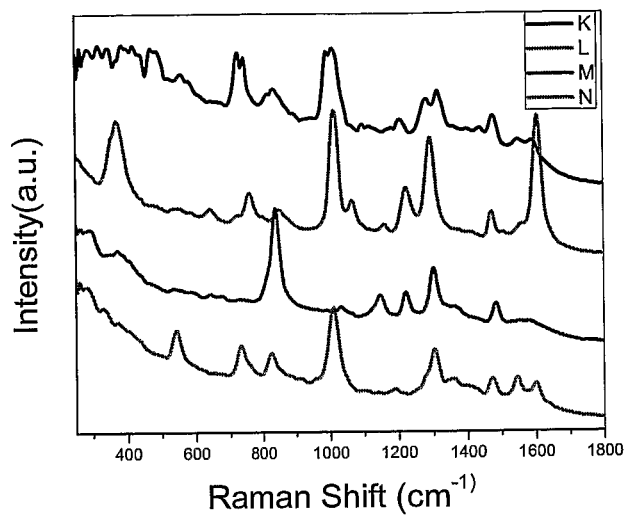
FIG. 7b shows the SERS signal of an AuNP encapsulated with an amphiphilic polymer and coated with (K) 4,4'-dimethoxy-2,2'-bipyridine, (L) 2,2'-bipyridine, (M) 5,5'-dimethyl-2,2'-bipyridine, (N) 4,4'-dimethyl-2,2'-bipyridine.
Figure 7C:
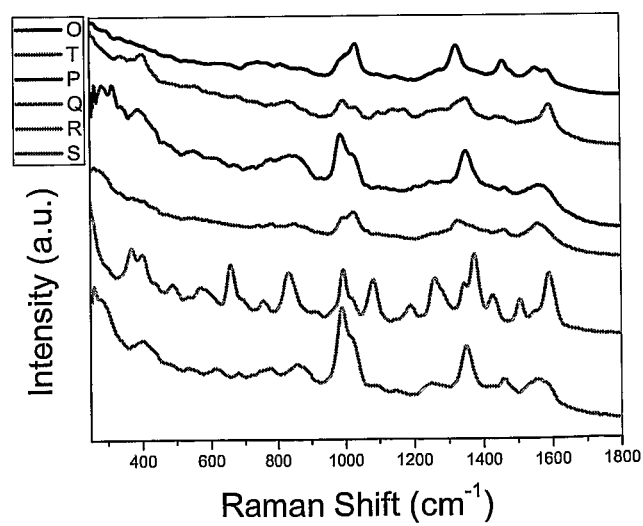
FIG. 7c shows the SERS signal of an AuNP encapsulated with an amphiphilic polymer and coated with (O) 2,2';6',2"-terpyridine, (P) 4'(4-methyl-phenyl)-2,2';6',2"-terpyridine, (Q) 4'(4-chloro-phenyl)-2,2';6',2"-terpyridine, (R) 4,4',4"-tri-tert-butyl-2,2';6',2"-terpyridine, (S) 4-phenyl-2,2';6',2"-terpyridine, (T) 4'(4-nitro-phenyl)-2,2';6',2"-terpyridine.

Encapsulation of Au NPs Coated with Raman Active Molecules Shown in FIG. 6 with $PS_{154}$-b-$PAA_{60}$ In a typical reaction, 6 mL of AuNP solution ($d_{av}$=60 nm) was concentrated to 13 µL by centrifugation at 6000 g for 10 min. Then $H_2O$ (187 µL) was added to the deep red suspension collected at the bottom of Eppendorf tubes, followed by addition of 40 µL of a Raman active molecule as shown in FIG. 6 in DMF (2 mg/mL). The mixture was immediately added into 800 µL DMF containing 80 µL $PS_{154}$-b-$PAA_{60}$ (8 mg/mL in DMF). The mixture was heated to 110° C. for 2 h and then allowed to slowly cool down in the oil bath until it reached room temperature. The final solution was deep red and remained stable at room temperature for months.

The above nanoparticles were purified by centrifugation (6000 g, 10 min) to remove DMF, empty micelles, and excess ligand. The resulting AuNPs coated with a Raman active molecule as shown in FIG. 6 and encapsulated in a layer of $PS_{154}$-b-$PAA_{60}$ were collected at the bottom of the tube. The NPs were diluted with 1500 µL $H_2O$, and purified by centrifugation at 6000 g for 10 min. This purification process was typically repeated twice to obtain samples free of DMF and empty micelles. And the purified NPs were dispersed in 1500 µL $H_2O$ for Raman measurement.

Raman spectra were collected from the sample solution in a cuvette (pathlength 1.00 cm) on an R-3000HR spectrometer (Raman Systems, Inc, R-3000 series) using a red light-emitting diode (LED) laser (λ=785 nm) at 290 mW.

Encapsulation of 4-ethylbezenethiol-Functionalized AuNP Aggregates

In a typical reaction, 2×1.5 mL of AuNPs solution ($d_{av}$=14.6 nm, 2.94 nM) was concentrated to ~10 µL by centrifugation at 16000 g for 15 min. To the deep red suspension collected at the bottom of Eppendorf tube, 300 µL DMF was added, followed by 20 µL of 4-ethylbenzenethiol in DMF (8 mg/mL). The mixture was added to a vial which contains 10 µL NaOH (2.5 mM) and 250 µL DMF. After that, a solution contains 10 µL HCl (5 mM), 60 µL $H_2O$ ($V_{HCl}+V_{H2O}$=70 µL) and 250 µL DMF was added, and the mixture was incubated again at 60° C. for 2 h. ([HCl]=0.06 mM) Aggregations of 15 nm AuNPs were formed at this stage. Different aggregation size can be simply tuned by changing the concentration of HCl (0.06 mM for FIG. 8A and 0.12 mM for FIG. 8B). To encapsulate the aggregated AuNPs, 80 µL $PS_{154}PAA_{60}$ solution (8 mg/mL in DMF) and 110 µL $H_2O$ was added in sequence. The total volume of the final mixture solution was 1100 µL, where the DMF/$H_2O$ volume ratio was 4.5; [$PS_{154}PAA_{60}$]= 28.5 µM, [4-ethylbenzenethiol]=6.31 µM. The mixture was heated to 110° C. for 2 h and then allowed to slowly cool down in the oil bath until room temperature was reached.

Preparation of Anisotropic Encapsulation of Metal NPs

In general, encapsulation of metal NPs, such as AuNPs can be carried out as follows. In case of AuNPs, AuNP's were prepared following literature procedures by sodium citrate reduction of $HAuCl_4$ as already described above (Frens, G., 1973, supra). AuNPs (25.7±1.9 nm, 3 mL) solution was centrifuged to a volume of about 15 µL using 16000 g for 15 min. The deep red solution collected was then diluted by water (167 µL) and then added to 818 µL of an organic solvent, such as DMF solution which was prepared by mixing an amphiphilic polymer, such as $PS_{154}$-block- PAA$_{60}$ (80 µL, 8 mg/mL in DMF), a ligand comprising a binding moiety for binding to the metal nanoparticle ligand, such as ethanethiol. (20 µL, 13.9 mM in DMF) and an organic solvent, such as DMF (718 µL). A Raman active molecule, such as 2-naphthalenthiol (80 µL, 2 mg/mL in EtOH) was then finally added to the reaction mixture giving a total volume of 1.08 mL in final mixture, where V$_{organic\ solvent}$/V$_{H2O}$=4.5. The mixture was heated at 110° C. for 2 hrs, and then allowed to cool down gradually till room temperature. Similar procedures were used for other ligand combinations (see FIG. 10).

Preparation of Anisotropic Encapsulated AuNP Chains with an Amphiphilic Polymer

AuNPs (20 nm, 3 mL) solution was centrifuged to a volume of 15 µL using 16000 g for 15 min. The deep red solution collected was then diluted to 72.5 µL and HCl (17.5 µL, 10 mM) was added to the mixture. The mixture was then added to 680 µL of DMF solution; ethanethiol (20 µL, 13.9 mM in DMF) and 2-naphthalenthiol (20 µL, 3 mg/ml in DMF). The mixture was incubated at 60° C. for 2 h to induce aggregation and further sonicated for another 2 h. Presumably, coating of the Au surface with 4-naphthalenethiol reduces the surface charges, while the addition of HCl increases the ionic strength of the solution. These two factors led to linear aggregation of AuNPs. After incubation, PS$_{154}$-block-PAA$_{60}$ (80 µL, 8 mg/mL in DMF) and H$_2$O (110 µL) was then added to the reaction mixture. The final mixture was heated at 110° C. for 2 h to encapsulate the aggregates and allowed to cool down gradually till room temperature. FIG. 10C shows a TEM image of the obtained anisotropically encapsulated and Raman label coated nanoparticles.

The invention claimed is:

1. A Raman active composite material comprising:
a metal particle aggregate formed from two or more metal particles, wherein the two or more metal particles comprise gold;
a coating layer of a hydrophobic Raman active molecule and ethanethiol, for binding to the two or more metal particles of the metal particle aggregate; and
an anisotropically encapsulating layer of an amphiphilic diblock copolymer, wherein an hydrophobic portion of the amphiphilic diblock copolymer interacts with the hydrophobic Raman active molecule to anisotropically encapsulate the metal particle aggregate comprising the two or more metal particles having the coating layer of the Raman active molecule and ethanethiol, and
wherein the diblock copolymer is selected from the group consisting of poly(acrylic acid-block-methyl methacrylate), poly(methyl methacrylate-block-sodium acrylate), poly(t-butyl methacrylate-block-ethylene oxide), poly(methyl methacrylate-block-sodium methacrylate), poly (methyl methacrylate-block-N-methyl-4-vinyl pyridinium iodide), poly(methyl methacrylate-block-N,N-dimethyl acrylamide), poly(butadiene-block-methacrylate acid and sodium salt), poly (butadiene(1,2 addition)-block-acrylic acid), poly (butadiene(1,2 addition)-block-sodium acrylate), poly (butadiene(1,4 addition)-block-acrylic acid), poly (butadiene(1,4 addition)-block-sodium acrylate), poly (butadiene(1,4 addition)-block-ethylene oxide), poly (butadiene(1,2 addition)-block-ethylene oxide), poly (styrene-block-acrylic acid), poly(styrene-block-acrylamide), poly(styrene-block-cesium acrylate), poly (styrene-block-sodium acrylate), poly(styrene-block-ethylene oxide), poly(styrene-block-methacrylic acid), and poly(styrene-block-sodium methacrylate).

2. The Raman active composite material according to claim 1, wherein the Raman active molecule is selected from the group consisting of:

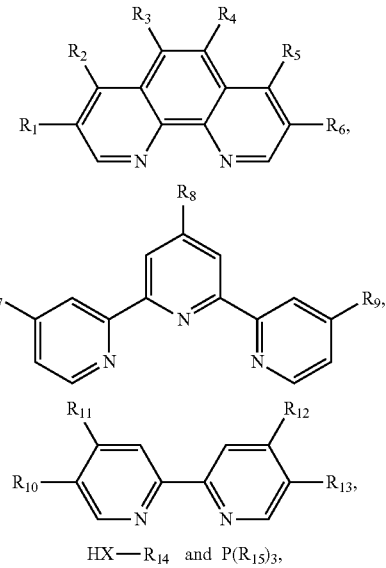

HX—R$_{14}$ and P(R$_{15}$)$_3$, wherein R$_1$ to R$_{13}$ are independently selected from hydrogen, optionally substituted alkyl, optionally substituted aryl, alkoxy, aryl, halogen, NO$_2$, CN, OH, carbonyl, amino or silyl; R$_{14}$ to R$_{15}$ are selected from optionally substituted alkyl, alkoxy, optionally substituted aryl and optionally substituted aryloxy; x is S or O.

3. The Raman active composite material according to claim 2, wherein the Raman molecule is selected from the group consisting of

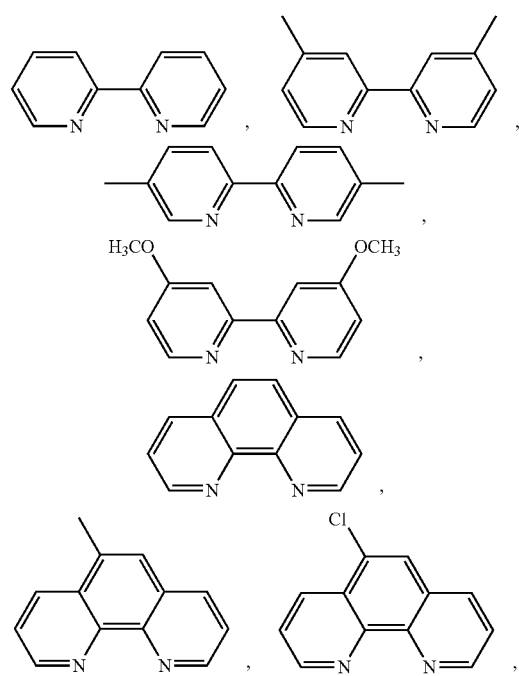

-continued
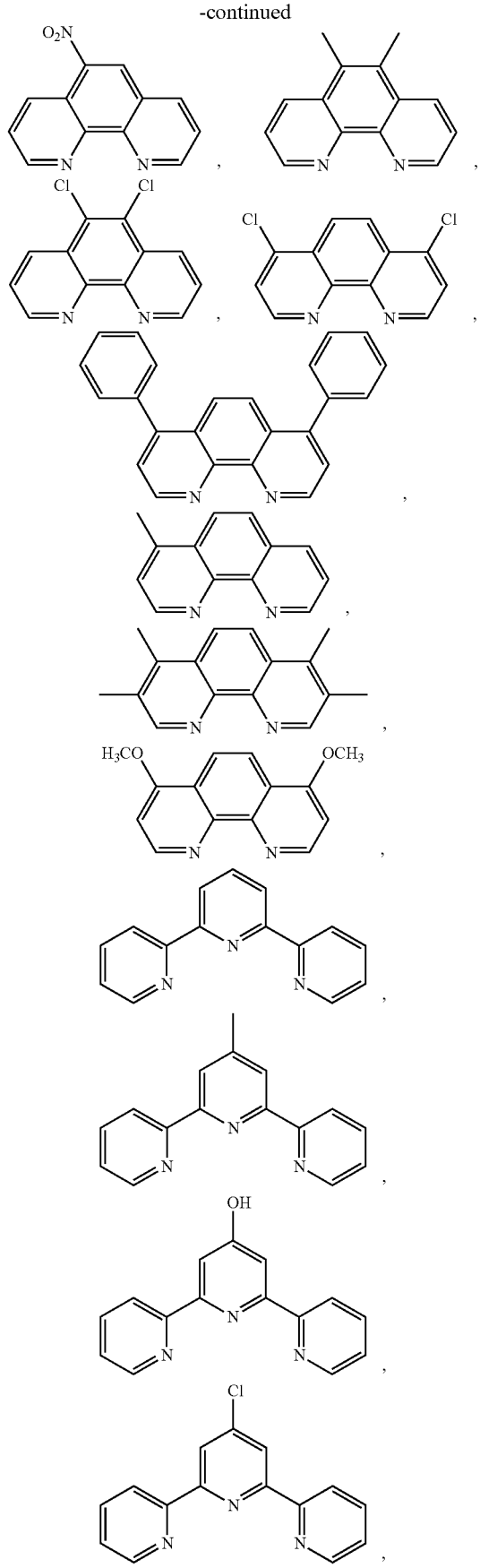
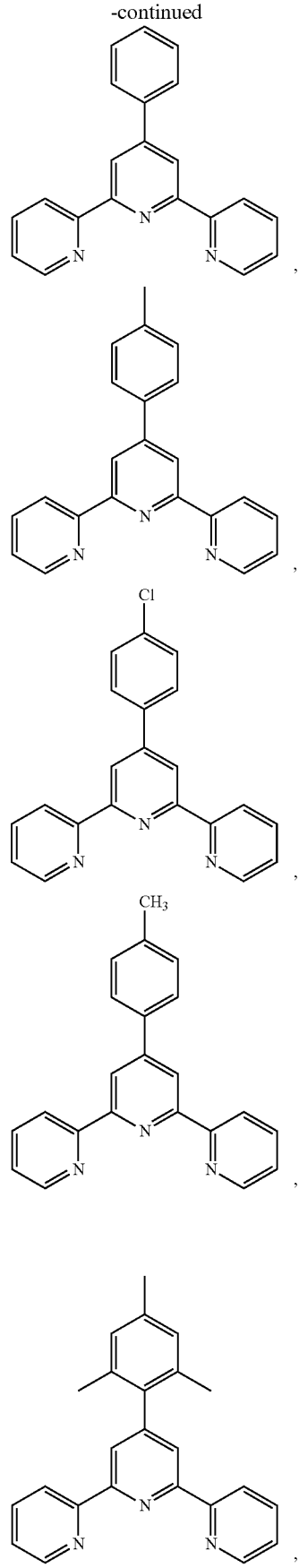

-continued

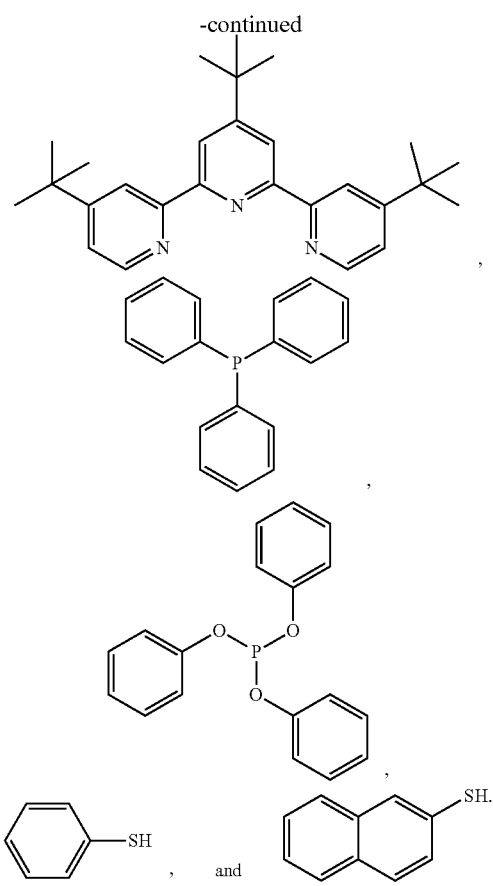

, and

4. The Raman active composite material according to claim 1, wherein the two or more metal particles comprise a metal particle having at least one dimension in the micrometer range.

5. The Raman active composite material according to claim 1, wherein the two or more metal particles comprise a metal particle having at least one dimension in the nanometer range.

6. The Raman active composite material according to claim 5, wherein the two or more metal particles comprise a nanoparticle having a size in at least one dimension of between about 5 nm to about 900 nm.

7. The Raman active composite material according to claim 5, wherein the two or more metal particles comprise a metal particle selected from the group consisting of a nanosphere, a nanocube, a nanorod, a nanotube and a nanowire.

8. The Raman active composite material according to claim 1, further comprising a recognition moiety which is bound to the Raman active molecule or the amphiphilic diblock copolymer.

9. The Raman active composite material according to claim 8, wherein the recognition moiety is selected from the group consisting of a nucleotide, a nucleic acid molecule, a peptide, a protein, a lipid, a carbohydrate, a drug, a drug precursor, a drug candidate molecule, a drug metabolite, a vitamin, a synthetic polymer, a receptor ligand, a metabolite, an immunoglobulin, a fragment of an immunoglobulin, a domain antibody, a proteinaceous binding molecule with antibody-like functions, a glubody, a protein based on the ankyrin scaffold or the crystalline scaffold, an AdNectin, a tetranectin, an avimers and a peptoid.

10. The method of manufacturing a Raman active composite material according to claim 1, wherein the method comprises:
   providing a solution comprising two or more metal particles comprising gold, an organic solvent, an amphiphilic diblock copolymer, ethanethiol and a Raman active molecule;
   inducing aggregation of the two or more metal particles to form a metal particle aggregate in the solution;
   incubating the solution for a time sufficient to allow self-assembly of an amphiphilic diblock copolymer shell around the metal particle aggregate; and
   cooling the solution.

11. The method of claim 10, wherein the step of providing the solution comprises:
   mixing two or more metal particles comprising gold with a solution comprising an organic solvent, an amphiphilic diblock copolymer, and ethanethiol, for binding to each of the two or more metal particles; and
   adding a Raman active molecule to the solution.

12. The method of claim 10, wherein the step of providing the solution comprises:
   mixing an acidic solution of two or more metal particles comprising gold with a solution comprising an organic solvent, a Raman active molecule, and ethanethiol, for binding to each of the two or more metal particles;
   incubating the solution; and
   adding an amphiphilic diblock copolymer to the solution.

13. The method according to claim 10, wherein the organic solvent is a polar solvent.

14. The method according to claim 13, wherein the polar solvent is selected from the group consisting of dimethylformamide (DMF), dimethyl sulfoxide, dioxane and hexamethylphosphorotriamide, tetrahydrofuran and mixtures thereof.

15. The method according to claim 10, wherein the step of inducing aggregation of the two or more metal particles in the solution is carried out at a temperature between about 30° C. to about 100° C.

16. The method according to claim 12, wherein water is added to the solution after the amphiphilic diblock copolymer was added to the solution.

17. The method according to claim 16, wherein the final volume ratio of organic solvent to water in the solution is between about 1:0.1 to about 10:1.

18. The method according to claim 10, wherein the step of incubating the solution is carried out at a temperature between about 0° C. to about 200° C.

19. The method according to claim 10, wherein the solution is heated for a period of time between about 1 min to 5 hours in the step of incubating the solution for a time sufficient to allow self-assembly of an amphiphilic diblock copolymer shell around the metal particle aggregate.

* * * * *